(12) United States Patent
Charmot et al.

(10) Patent No.: US 7,488,495 B2
(45) Date of Patent: *Feb. 10, 2009

(54) ION BINDING POLYMERS AND USES THEREOF

(75) Inventors: Dominique Charmot, Campbell, CA (US); Han Ting Chang, Livermore, CA (US); Gerrit Klaerner, San Jose, CA (US); Michael James Cope, Berkeley, CA (US); Mingjun Liu, Campbell, CA (US); Futian Liu, Mountain View, CA (US); Jerry Buysse, Los Altos, CA (US); Eric Connor, Los Gatos, CA (US); Tony Kwok-Kong Mong, Hsinchu (TW); Jun Shao, Fremont, CA (US); Deidre Madsen, Sunnyvale, CA (US)

(73) Assignee: Relypsa, Inc., Santa Clara, CA (US)

( * ) Notice: Subject to any disclaimer, the term of this patent is extended or adjusted under 35 U.S.C. 154(b) by 560 days.

This patent is subject to a terminal disclaimer.

(21) Appl. No.: 10/965,274

(22) Filed: Oct. 13, 2004

(65) Prior Publication Data

US 2005/0220751 A1 Oct. 6, 2005

Related U.S. Application Data

(63) Continuation-in-part of application No. 10/814,527, filed on Mar. 30, 2004, and a continuation-in-part of application No. 10/814,749, filed on Mar. 30, 2004, and a continuation-in-part of application No. 10/813,872, filed on Mar. 30, 2004.

(51) Int. Cl.
*A61K 9/20* (2006.01)
*A61K 9/32* (2006.01)

(52) U.S. Cl. .................. 424/464; 424/400; 424/483

(58) Field of Classification Search ................. 424/400, 424/464, 483
See application file for complete search history.

(56) References Cited

U.S. PATENT DOCUMENTS 2,611,730 A 9/1952 Heming et al.

(Continued)

FOREIGN PATENT DOCUMENTS

EP 0349453 A1 4/1989

(Continued)

OTHER PUBLICATIONS

Berlyne, G.M., et al. "Cation exchange resins in hyperkalaemic renal failure." (1967) Israel J Med Sci 3(1): 45-52.

(Continued)

*Primary Examiner*—Johann R. Richter
*Assistant Examiner*—Konata M George
(74) *Attorney, Agent, or Firm*—Senniger Powers LLP

(57) ABSTRACT

The present invention provides methods and compositions for the treatment of ion imbalances. In particular, the invention provides compositions comprising potassium binding polymers and pharmaceutical compositions thereof. Methods of use of the polymeric and pharmaceutical compositions for therapeutic and/or prophylactic benefits are disclosed herein. Examples of these methods include the treatment of hyperkalemia, such as hyperkalemia caused by renal failure and/or the use of hyperkalemia causing drugs.

20 Claims, 6 Drawing Sheets

U.S. PATENT DOCUMENTS

| | | | |
|---|---|---|---|
| 2,909,462 | A | 10/1959 | Warfield et al. |
| 3,499,960 | A | 3/1970 | Macek et al. |
| 3,974,272 | A | 8/1976 | Polli et al. |
| 4,143,130 | A | 3/1979 | Imondi |
| 4,470,975 | A | 9/1984 | Berger |
| 4,605,701 | A | 8/1986 | Harada et al. |
| 4,747,881 | A | 5/1988 | Shaw et al. |
| 4,837,015 | A | 6/1989 | Olsen |
| 4,902,501 | A | 2/1990 | Bandi et al. |
| 4,942,205 | A | 7/1990 | Ohmori et al. |
| 5,051,253 | A | 9/1991 | Lloyd-Jones |
| 5,091,175 | A | 2/1992 | Imondi et al. |
| 5,141,927 | A | 8/1992 | Krotkiewski |
| 5,186,937 | A | 2/1993 | Sparks et al. |
| 5,281,631 | A | 1/1994 | Horwitz |
| 5,374,422 | A | 12/1994 | Pierre |
| 5,487,888 | A | 1/1996 | Mandeville, III et al. |
| 5,607,669 | A | 3/1997 | Mandeville |
| 5,618,530 | A | 4/1997 | Mandeville, III et al. |
| 5,633,344 | A | 5/1997 | Figuly |
| 5,667,775 | A | 9/1997 | Holmes-Farley et al. |
| 5,679,717 | A | 10/1997 | Mandeville, III et al. |
| 5,693,675 | A | 12/1997 | Mandeville, III et al. |
| 5,702,696 | A | 12/1997 | Mandeville, III et al. |
| 5,718,920 | A | 2/1998 | Notenbomer |
| 5,935,599 | A | 8/1999 | Dadey |
| 6,294,163 | B1 | 9/2001 | Dhal |
| 6,881,484 | B2 | 4/2005 | Kataoka et al. |
| 2002/0054903 | A1 | 5/2002 | Tyler et al. |
| 2002/0146386 | A1 | 10/2002 | Simon et al. |
| 2003/0027789 | A1 | 2/2003 | Yamaoka et al. |
| 2003/0065090 | A1 | 4/2003 | Kelly et al. |
| 2004/0166156 | A1 | 8/2004 | Tyler et al. |
| 2004/0251204 | A1 | 12/2004 | Paananen et al. |
| 2005/0036983 | A1 | 2/2005 | Simon et al. |
| 2005/0220752 | A1* | 10/2005 | Charmot et al. ............ 424/78.1 |
| 2005/0220889 | A1* | 10/2005 | Charmot et al. ............ 424/490 |
| 2005/0220890 | A1 | 10/2005 | Charmot et al. |
| 2006/0024336 | A1 | 2/2006 | Charmot et al. |

FOREIGN PATENT DOCUMENTS

| | | |
|---|---|---|
| EP | 0730494 B1 | 2/1998 |
| JP | 1998059851 A | 3/1998 |
| JP | 1998130154 A | 5/1998 |
| NL | 0 730 494 B1 * | 2/1998 |
| WO | WO 82/00257 | 2/1982 |
| WO | WO 92/10522 | 6/1992 |
| WO | WO 94/27619 | 12/1994 |
| WO | WO 95/14531 | 6/1995 |
| WO | 9749387 | 12/1997 |
| WO | WO 97/49736 | 12/1997 |
| WO | 0040224 | 7/2000 |
| WO | WO 01/51063 A1 | 7/2001 |
| WO | WO 02/12160 A1 | 2/2002 |
| WO | WO 02/40039 A2 | 5/2002 |
| WO | WO 02/062356 A2 | 8/2002 |
| WO | WO 2005/065291 A2 | 7/2005 |

OTHER PUBLICATIONS

Chourasia, M.K., et al., "Pharmaceutical approaches to colon targeted drug delivery systems." (2003) J. Pharm Pharm Sci 6(1): 33-66.

Corcoran, A.C., et al., "Controlled observations on the effect of low sodium dietotherapy in essential hypertension." (1951) Circulation 3(1): 1-16.

Danowski, T.S., et al., "Changes in fecal and serum constituents during ingestion of cation and anion exchangers." (1953) Ann N Y Acad Sci. 57(3): 273-9.

Emerson, K., Jr., et al., "The role of the gastro-intestinal tract in the adaptation of the body to the prevention of sodium depletion by cation exchange resins." (1953) Ann N Y Acad Sci. 57(3): 280-90.

Emmett, M., et al. "Effect of Three Laxatives and a Cation Exchange Resin on Fecal Sodium and Potassium Excretion." (1995) Gastroenterology 108(3): 752-60.

Evans, B.M., et al. "Ion-exchange resins in the treatment of anuria." (1953) Lancet 265(6790): 791-5.

Field, H., Jr., et al., "Electrolyte changes in ileal contents and in feces during restriction of dietary sodium with and without the administration of cation-exchange resin." (1955) Circulation 12(4): 625-9.

Field, H., Jr., et.al., "Mechanisms regulating the retention of sodium in the feces by cation-exchange resin: release of base from the resin by bacterial fermentation in the terminal ileum." (1958) J Lab Clin Med 51(2): 178-84.

Fourman, P. "Capacity of a cationic exchange resin (zeo-karb 225) in vivo." (1953) British Medical Journal 1(4809): 544-6.

Greenman, L., et al. "Biochemical changes accompanying the ingestion of a carboxylic cation exchanger in the hydrogen, ammonium, sodium, potassium, or calcium form." (1951) J Clin Invest. 30(9): 995-1008.

Gruy-Kapral, C., et al., "Effect of single dose resin-cathartic therapy on serum potassium concentration in patients with end-stage renal disease." (1998) J Am Soc Nephrol 9(10): 1924-30.

Harthon, J.G.L., et al., "A Case of Uremia and Hyperpotassemia Treated With Sulphonic Cation-Exchange Resin" (1952) Acta Med Scan., 144(3): 230-6.

Heming A. E., et al., "Considerations in the selection of cation exchange resins for therapeutic use." (1953) Ann N Y Acad Sci. 57(3):239-51.

Irwin, L., et al. "The effect of a cation exchange resin on electrolyte balance and its use in edematous states." (1949) J Clin Invest. 28(6, Pt. 2): 1403-11.

Kohlstaedt, K.G., et al., "Clinical experience with mixtures of anion and cation exchange resins." (1953) Ann N Y Acad Sci. 57(3): 260-72.

Mason N.S., et al., "A new ion exchanger with high in vivo sodium capacity." (1985) Kidney Int Suppl. 28(17): S178-182.

Mateer, F.M., et al., "Sodium Restriction and Cation Exchange Resin Therapy in Nephrotic Children" (1951) J Clin Invest. 30(9): 1018-25.

McChesney, E.W. "Effects of long-term feeding of sulfonic ion exchange resin on the growth and mineral metabolism of rats." (1954) Am J Physiol. 177(3):395-400.

McChesney, E.W., et al., "Some aspects of cation exchange resins as therapeutic agents for sodium removal." (1953) Ann N Y Acad Sci. 57(3):252-9.

Moustafine R.I., et al., "Characteristics of interpolyelectrolyte complexes of Eudragit E 100 with sodium alginate." (2005) Int J Pharm 294(1-2): 113-20.

Root, M.A., "Comparison of the in vivo sodium-removing activity of various types of ion exchange resins in rats." (1953) J Lab Clin Med 42(3): 430-7.

Ross, E.J., et al. "Observations on cation exchange resins in the small and large intestines." (1954) Clin Sci 13(4): 555-66.

Tust, R. H., et al., "The Effects of Malethamer on the Excretion and Plasma Levels of Sodium, Potassium, and Chloride (34990)" (1970) Proc Soc Exp Biol Med. 135(1): 72-6.

Wrong, O., et al., "The electrolyte content faeces." (1965) Proc R. Soc Med 58(12): 1007-9.

Coli, L. et al. 1992. Phosphate Removal by Resin Hemoperfusion Efficacy and Biocompatibility of a New Exchange Resin. *Biomaterials, Artificial Cells, and Immobilization Biotechnology.* 20(5): 1153-1163.

Forrest, M. Laird, et al. 2003. A Degradable Polyethylenimine Derivative with Low Toxicity for Highly Efficient Gene Delivery. *Bioconjugate Chem.* 14(5): 934-940.

Koping-Hoggard, M. et al. 2001. Chitosan as a nonviral gene delivery system. Structure-property relationships and characteristics compared with polyethylenimine in vitro and after lung administration in vivo. *Gene Therapy.* 8: 1108-1121.

Thomas, Mini, etal. 2005. Cross-linked Small Polyethylenimines: While Still Nontoxic, Deliver DNA Efficiently to Mammalian Cells in Vitro and in Vivo. *Pharmaceutical Research.* 22(3): 373-380.

Friedman, Eli A., Clinical Aspects of Uremia and Dialysis/ Sorbent Therapy in Uremia 671-687. (Shaul G. Massry & Alvin L. Sellers eds., 1976).

Friedman, Eli A., et al. 1976. Combined oxystarch-charcoal trial in uremia: Sorbent-induced reduction in serum cholesterol. *Kidney International.* 10:S-273-S-276.

Imondi, A.R., et al: 1981. Gastrointestinal Sorbents for the Treatment of Uremia. I. Lightly Cross-Linked Carboxyvinyl Polymers. *Ann Nutr Metabol.* 25(5): 311-319.

Thies, Curt. 1982. Microcapsules as drug delivery devices. *Crit Rev Biomed Eng.* 8(4): 335-383.

Gerstman, et al., Use Of Sodium Polystyrene Sulfonate In Sorbitol In The United States, 1985-1989, vol. XVIII, No. 5 (Nov.), 1991, pp. 619-621, American Journal of Kidney Diseases.

Kim, et al., Therapeutic Approach to Hyperkalemia, Nephron, 2002, 92 (suppl 1), pp. 33-40, Division of Nephrology, Department of Internal Medicine, Hanyang University Kuri Hospital, Kuri, Korea.

Agarwal, et al., Pathophysiology of Potassium Absorption and Secretion by the Human Intestine, Gastroenterology, 1994, vol. 107, pp. 548-571, American Gastroenterological Association.

Ross, et al., Observations on Cation Exchange Resins in the Small and Large Intestines, 1954, pp. 555-566, Medical Unite, University College Hospital Medical School, London, W.C.1.

Salas-Coll, et al., Potassium transport across the distal colon in man, Clinical Science and Molecular Medicine, 1976, vol. 51, pp. 287-296.

Spencer, et al., Cation Exchange In The Gastrointestinal Tract, 1954, pp. 603-606, Medical Unit, University College Hospital Medical School, London, W.C.1.

Wrong, O.M., The Role of the Human Colon in Homeostasis, The Human Colon, pp. 192-215.

Wrong, et al., In Vivo Dialysis of Faeces As A Method Of Stool Analysis, Clinical Science, 1965, vol. 28, pp. 357-375.

Dai, et al, Controlling Ion Transport through Mulitlayer Polyelectrolyte Membranes by Derivatization with Photolabile Functional Groups, Macromolecules, 2002, vol. 35, pp. 3164-3170, American Chemical Society.

Estrela-Lopis, et al., Sans Studies of Polyelectrolyte Multilayers on Colloidal Templates, Langmuir, 2002, vol. 18, pp. 7861-7866, American Chemical Society.

Meszaros, et al., Adsorption of Poly(ethyleneimine) on Silica Surfaces: Effect of pH on the Reversibility of Adsorption, Langmuir, 2004, vol. 20, pp. 5026-5029, American Chemical Society.

Picart, et al., Microinterferometric Study of the Structure, Interfacial Potential, and Viscoelastic Properties of Polyelectrolyte Multilayer Films on a Planar Substrate, J. Phys. Chem. B, 2004, vol. 108, pp. 7196-7205, American Chemical Society.

EP Search Report for counterpart foreign Application No. EP 05732849 dated May 8, 2007.

Cuna, M. et al., Controlled-release liquid suspensions based on ion-exchange particles entrapped within acrylic microcapusles, International Journal of Pharmaceutics, 2000, vol. 199, pp. 151-158, Elsevier Science.

Ichikawa, H. et al., Use of ion-exchange resins to prepare 100 μm-sized microcapsules with prolonged drug-release by the Wurster process, International Journal of Pharmaceutics, 2001, vol. 216, pp. 67-76, Elsevier Science.

EP Search Report for counterpart foreign Application No. 05731099 dated May 8, 2007, 3 pages.

Blake, J., M.D., et al., "Differential Effects of Direct Antagonism of AII Compared to ACE Inhibitors on Serum Potassium Levels and Azotemia in Patients with Severe Congestive Heart Failure," Congestive Heart Failure, Jul./Aug. 2000, pp. 193-196, vol. 6, No. 4, CHF, Inc., Darien, Connecticut.

Johnson, K., et al., "Sodium Polystyrene Sulfonate Resin Candy for Control of Potassium in Chronic Dialysis Patients," Clinical Nephrology, 1976, pp. 266-268, vol. 5, No. 6.

\* cited by examiner

ION BINDING POLYMERS AND USES THEREOF

CROSS-REFERENCE

This application is a continuation-in-part application of U.S. application Ser. No. 10/814,527, filed Mar. 30, 2004; U.S. application Ser. No. 10/814,749, filed Mar. 30, 2004; and U.S. application Ser. No. 10/813,872, filed Mar. 30, 2004 which are incorporated herein by reference in their entirety.

BACKGROUND OF THE INVENTION

Potassium ($K^+$) is the most abundant intracellular cation, comprising ~35-40 mEq/kg in humans. See Agarwal, R, et al. (1994) Gastroenterology 107: 548-571; Mandal, A K (1997) Med Clin North Am 81: 611-639. Only 1.5-2.5% of this is extracellular. Potassium is obtained through the diet, mainly through vegetables, fruits, meats and dairy products, with certain food such as potatoes, beans, bananas, beef and turkey being especially rich in this element. See Hunt, C D and Meacham, S L (2001) J Am Diet Assoc 101: 1058-1060; Hazell, T (1985) World Rev Nutr Diet 46: 1-123. In the US, intake is ~80 mEq/day. About 80% of this intake is absorbed from the gastrointestinal tract and excreted in the urine, with the balance excreted in sweat and feces. Thus, potassium homeostasis is maintained predominantly through the regulation of renal excretion. Where renal excretion of $K^+$ is impaired, elevated serum $K^+$ levels will occur. Hyperkalemia is a condition wherein serum potassium is greater than about 5.0 mEq/L.

While mild hyperkalemia, defined as serum potassium of about 5.0-6 mEq/L, is not normally life threatening, moderate to severe hyperkalemia (with serum potassium greater than about 6.1 mEq/L) can have grave consequences. Cardiac arrythmias and altered ECG waveforms are diagnostic of hyperkalemia. See Schwartz, M W (1987) Am J Nurs 87: 1292-1299. When serum potassium levels increases above about 9 mEq/L, atrioventricular dissociation, ventricular tachycardia, or ventricular fibrillation can occur.

Hyperkalemia is rare in the general population of healthy individuals. However, certain groups definitely exhibit a higher incidence of hyperkalemia. In patients who are hospitalized, the incidence of hyperkalemia ranges from about 1-10%, depending on the definition of hyperkalemia. Patients at the extremes of life, either premature or elderly, are at high risk. The presence of decreased renal function, genitourinary disease, cancer, severe diabetes, and polypharmacy can also predispose patients to hyperkalemia.

Most of the current treatment options for hyperkalemia are limited to use in hospitals. For example, exchange resins, such as Kayexalate, are not suitable for outpatient or chronic treatment, due to the large doses necessary that leads to very low patient compliance, severe GI side effects and significant introduction of sodium (potentially causing hypematremia and related fluid retention and hypertension). Diuretics that can remove sodium and potassium from patients via the kidneys are often limited in their efficacy due to underlying kidney disease and frequently related diuretic resistance. Diuretics are also contraindicated in patients where a drop in blood pressure and volume depletion are undesired (e.g. CHF patients that in addition to suffering from low blood pressure are often on a combination of drugs such as ACE inhibitors and potassium sparing diuretics such as spironolactone that can induce hyperkalemia).

Overall, it would be desirable to obtain higher binding capacity materials for the treatment of hyperkalemia, such materials preferably having a greater binding in the physiological pH range for potassium, which are also non-degradable, non-absorbable and have decreased toxic effects.

SUMMARY OF THE INVENTION

The present invention provides compositions and methods for the removal of potassium ions from the gastro-intestinal tract. In one embodiment, an effective amount of a potassium binding polymer is administered to an animal subject, such as a human, the polymer being capable of binding and removing an average of 1.5 mmol of potassium per gm of polymer. In another embodiment, the polymer has an average in vitro binding capacity of greater than about 5 mmol/gm of polymer at a pH of greater than about 5.5. In another embodiment, the potassium binding polymer further comprises a shell that is physically or chemically attached to the polymer.

The potassium binding polymer is preferably a poly-fluoroacrylic acid polymer, a poly-difluoromaleic acid polymer, or a combination thereof. In other embodiments the polymer comprises 2-fluoroacrylic acid crosslinked with divinylbenzene, ethylene bisacrylamide, N,N'-bis(vinylsulfonylacetyl) ethylene diamine, 1,3-bis(vinylsulfonyl)2-propanol, vinylsulfone, N,N'-methylenebisacrylamide, epichlorohydrin or a combination thereof. Preferably, the shell comprises of copolymers of a vinylamine, ethyleneimine, propyleneimine, allylamine, methallylamine, vinylpyridines, alkyaminoalkyl (meth)acrylates, alkyaminoalkyl(meth)acrylamides, aminomethylstyrene, chitosan, adducts of aliphatic amine or aromatic amine with electrophile such as epichlorhydrine, alkylhalides or epoxides, and wherein the amine is optionally a quarternized form.

The compositions described herein are suitable for therapeutic and/or prophylactic use in the treatment of hyperkalemia. In one embodiment, the potassium binding compositions are used in combination with drugs that cause potassium retention such as potassium-sparing diuretics, angiotensin-converting enzyme inhibitors (ACEIs), non-steroidal anti-inflammatory drugs, heparin, or trimethoprim.

DETAILED DESCRIPTION OF THE INVENTION

Figure 1:
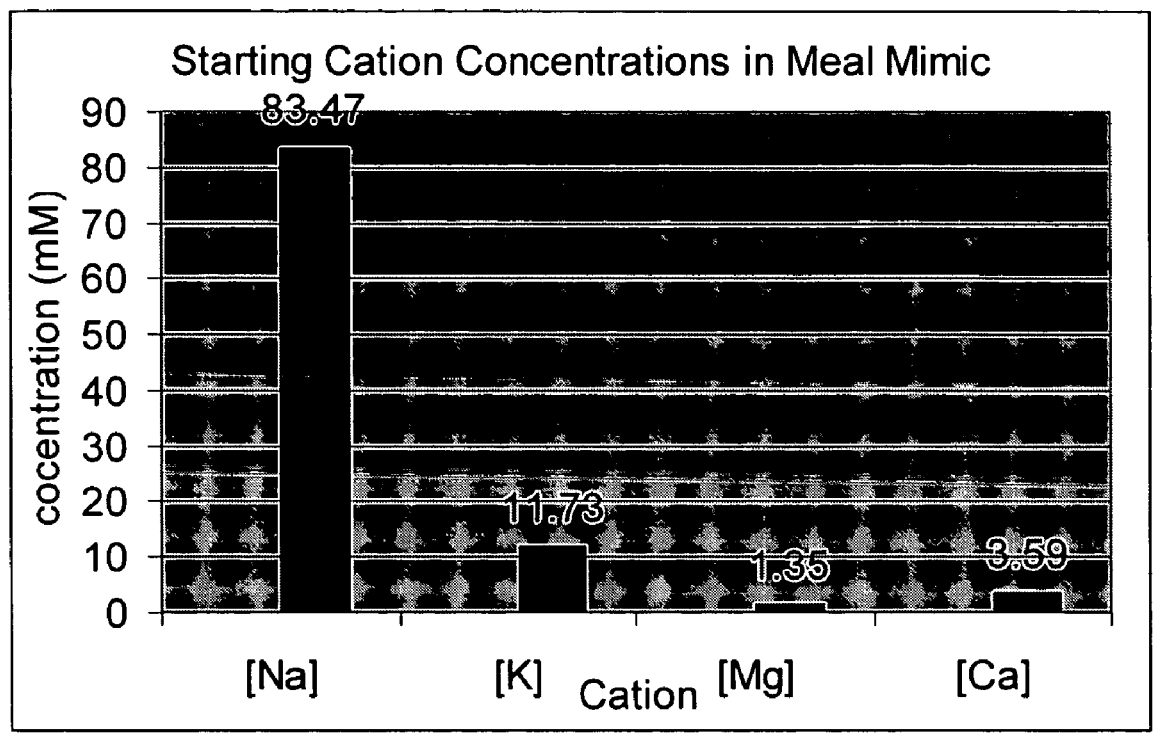
FIG. 1 depicts starting cation concentrations in a meal mimic.

The present invention provides methods, polymeric pharmaceutical compositions, and kits for the treatment of animal subjects. The terms "animal subject" and "animal" as used herein includes humans as well as other mammals. In particular, the present invention provides polymeric compositions for the removal of potassium ions. Preferably, these compositions are used for the removal of potassium ions from the gastrointestinal tract of animal subjects.

One aspect of the invention is a method of removing potassium ions with a potassium-binding polymeric composition. In one embodiment, the potassium-binding polymeric composition has high capacity and/or selectivity for binding potassium and does not significantly release the bound potassium in the gastrointestinal tract. It is preferred that the polymeric composition exhibit selective binding for potassium ions.

It is preferred that the polymeric compositions of the present invention exhibit high capacity and/or selectivity for potassium ions. The term "high capacity" as used herein encompasses an average in vivo binding of about 1.5 mmol or more of potassium per gm of polymer. Typically, this in vivo binding capacity is determined in a human. Techniques for determining in vivo potassium binding capacity in a human are well known in the art. For example, following administration of a potassium-binding polymer to a patient, the amount of potassium in the feces can be used to calculate the in vivo potassium binding capacity. The average in vivo binding is preferably calculated in a set of normal human subjects, this set being about 5 human subjects, preferably about 10 human subjects, even more preferably about 25 human subjects, and most preferably about 50 human subjects.

In some embodiments, the average in vivo potassium binding capacity can be equal to or more than about 1.5 mmol per gm of polymer in a human. Preferably the in vivo potassium binding capacity in a human is about 2 mmol or more per gm, more preferred is about 3 mmol or more per gm, even more preferred is about 4 mmol or more per gm, and most preferred is about 6 mmol or more per gm. In a preferred embodiment, the average in vivo potassium binding capacity in a human is about 2 mmol to about 6 mmol per gm in a human.

The capacity of the potassium binding polymers can also be determined in vitro. It is preferred that the in vitro potassium binding capacity is determined in conditions that mimic the physiological conditions of the gastro-intestinal tract, in particular the colon. In some embodiments, the in vitro potassium binding capacity is determined in solutions with a pH of about 5.5 or more. In various embodiments, in vitro potassium binding capacity in a pH of about 5.5 or more is equal to or more than 6 mmol per gm of polymer. A preferred range of in vitro potassium binding capacity in a pH of about 5.5 or more is about 6 mmol to about 12 mmol per gm of polymer. Preferably the in vitro potassium binding capacity in a pH of about 5.5 or more is equal to about 6 mmol or more per gm, more preferred is about 8 mmol or more per gm, even more preferred is about 10 mmol or more per gm, and most preferred is about 12 mmol or more per gm.

The higher capacity of the polymeric composition enables the administration of a lower dose of the composition. Typically the dose of the polymeric composition used to obtain the desired therapeutic and/or prophylactic benefits is about 0.5 gm/day to about 25 gm/day. Most preferred is about 15 gm/day or less. A preferred dose range is about 5 gm/day to about 20 gm/day, more preferred is about 5 gm/day to about 15 gm/day, even more preferred is about 10 gm/day to about 20 gm/day, and most preferred is about 10 gm/day to about 15 gm/day. Preferably the dose is administered about three times a day with meals.

It is also preferred that the compositions described herein retain a significant amount of the bound potassium. Preferably, the potassium is bound by the polymer in the colon and not released prior to excretion of the polymer in the feces. The term "significant amount" as used herein is not intended to mean that the entire amount of the bound potassium is retained. It is preferred that at least some of the bound potassium is retained, such that a therapeutic and/or prophylactic benefit is obtained. Preferred amounts of bound potassium that can be retained range from about 5% to about 100%. It is preferred that the polymeric compositions retain about 25% of the bound potassium, more preferred is about 50%, even more preferred is about 75% and most preferred is retention of about 100% of the bound potassium. The period of retention is preferred to be during the time that the composition is being used therapeutically and/or prophylactically. In the embodiment in which the composition is used to bind and remove potassium from the gastrointestinal tract, the retention period is the time of residence of the composition in the gastro-intestinal tract.

Preferably the potassium binding polymers are not absorbed from the gastro-intestinal tract. The term "non-absorbed" and its grammatical equivalents is not intended to mean that the entire amount of administered polymer is not absorbed. It is expected that certain amounts of the polymer may be absorbed. It is preferred that about 90% or more of the polymer is not absorbed, preferably about 95% or more is not absorbed, even more preferably about 97% or more is not absorbed, and most preferably about 98% or more of the polymer is not absorbed.

Potassium-Binding Polymers

In some embodiments, the potassium-binding polymers comprise acid groups in their protonated or ionized form, such as sulfonic ($-SO_3^-$), sulfuric ($-OSO_3^-$), carboxylic ($-CO_2^-$), phosphonic ($-PO_3^{--}$), phosphoric ($-(OPO_3^{--})$), or sulfamate ($-NHSO_3^-$). Preferably, the fraction of ionization of the acid groups is greater than about 75% at the physiological pH in the colon and the potassium binding capacity is greater than about 5 mmol/gm. Preferably the ionization of the acid groups is greater than about 80%, more preferably it is greater than about 90%, and most preferably it is about 100%. In certain embodiments the acid containing polymers contain more than one type of acid groups. In certain embodiments the acid containing polymers are administered in their anhydride form and generate the ionized form when contacted with physiological fluids.

In some other embodiments, a $pK_a$-decreasing group, preferably an electron-withdrawing substituent, is located adjacent to the acid group, preferably it is located in the alpha or beta position of the acid group. The preferred electron-withdrawing substituents are a hydroxyl group, an etheral group, an ester group, or an halide atom, and most preferably F. Preferred acid groups are sulfonic ($-SO_3^-$), sulfuric ($-OSO_3^-$), carboxylic ($-CO_2^-$), phosphonic ($-PO_3^{--}$), phosphoric ($-(OPO_3^{--})$), or sulfamate ($-NHSO_3^-$). Other preferred polymers result from the polymerization of alpha-fluoro acrylic acid, difluoromaleic acid, or an anhydride thereof.

Examples of other suitable monomers for potassium-binding polymers are included in Table 1.

TABLE 1
Examples of cation exchange moieities-structures & theoretical binding capacities
| | Molar mass per charge | Theoretical capacity | Fraction of titrable H @ pH 3 | Fraction of titrable H @ pH 6 | Expected Capacity @ pH 3 | Expected Capacity @ pH 6 |
|---|---|---|---|---|---|---|
| 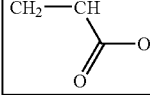 | 71 | 14.1 | 0.05 | .35 | 0.70 | 4.93 |
| 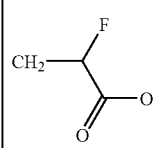 | 87 | 11.49 | 0.2 | 0.95 | 2.3 | 10.92 |
| 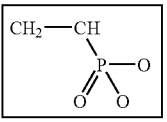 | 53 | 18.9 | 0.25 | 0.5 | 4.72 | 9.43 |
| 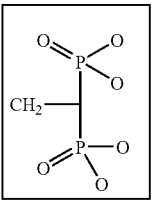 | 47.5 | 21.1 | 0.25 | 0.5 | 5.26 | 10.53 |
| 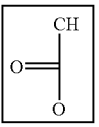 | 57 | 17.5 | 0.1 | 0.5 | 1.75 | 8.77 |
| 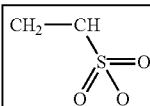 | 107 | 9.3 | 1 | 1 | 9.35 | 9.35 |
| 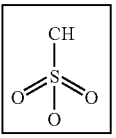 | 93 | 10.8 | 1 | 1 | 10.75 | 10.75 |
| 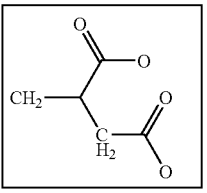 | 63 | 15.9 | 0 | 0.4 | 0 | 6.35 |
| 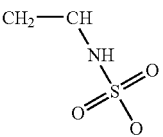 | 125 | 8 | 1 | 1 | 8 | 8 |

TABLE 1-continued

Examples of cation exchange moieities-structures & theoretical binding capacities

| | Molar mass per charge | Theoretical capacity | Fraction of titrable H @ pH 3 | Fraction of titrable H @ pH 6 | Expected Capacity @ pH 3 | Expected Capacity @ pH 6 |
|---|---|---|---|---|---|---|
| (styrene sulfonic acid structure) | 183 | 5.5 | 1 | 1 | 5.46 | 5.46 |
| (lactate structure) | 87 | 11.49 | .1 | .6 | 1.14 | 6.89 |

Other suitable cation exchange moieties include:

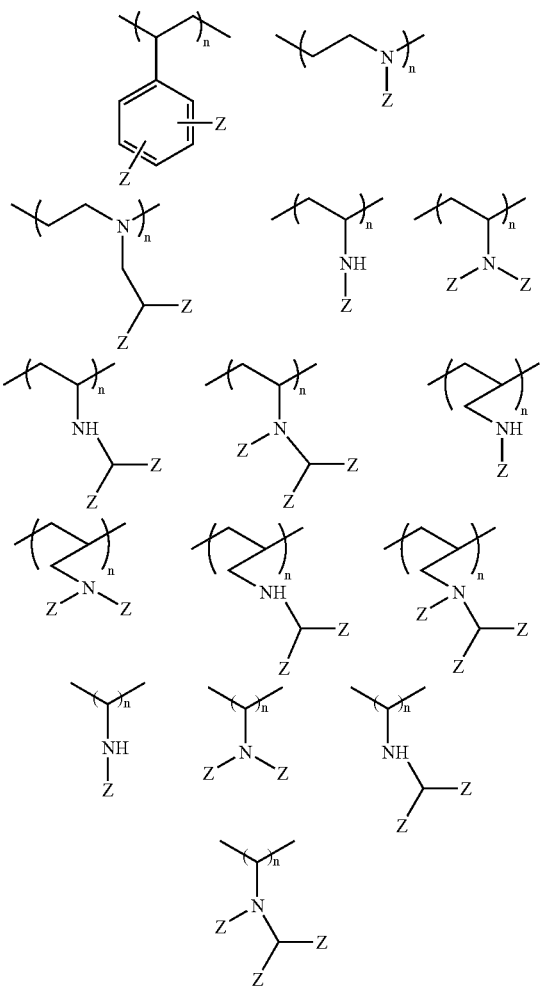

wherein is equal to or greater than one and Z represents either $SO_3H$ or $PO_3H$. Preferably n is about 50 or more, more preferably n is about 100 or more, even more preferred is n about 200 or more, and most preferred is n about 500 or more.

Suitable phosphonate monomers include vinyl phosphonate, vinyl 1,1 bis phosphonate, and ethylenic derivatives of phosphonocarboxylate esters, oligo(methylenephosphonates), and hydroxyethane-1,1-diphosphonic acid. Methods of synthesis of these monomers are well known in the art.

Sulfamic (i.e. when $Z=SO_3H$) or phosphoramidic (i.e. when $Z=PO_3H$) polymers can be obtained from amine polymers or monomer precursors treated with a sulfonating agent such as sulfur trioxide/amine adducts or a phosphonating agent such as $P_2O_5$, respectively. Typically, the acidic protons of phosphonic groups are exchangeable with cations, like sodium or potassium, at pH of about 6 to about 7.

Free radical polymers derived from monomers such as vinyl sulfonate, vinylphosphonate, or vinylsulfamate can also be used.

Preferred monomers for use herein are α-fluoroacrylate and difluoromaleic acid, α-fluoroacrylate being most preferred. This monomer can be prepared from a variety of routes, see for example, Gassen et al, J. Fluorine Chemistry, 55, (1991) 149-162, K F Pittman, C. U., M. Ueda, et al. (1980). *Macromolecules* 13(5): 1031-1036. Difluoromaleic acid is preferred by oxidation of fluoroaromatic compounds (Bogachev et al, Zhumal Organisheskoi Khimii, 1986, 22(12), 2578-83), or fluorinated furans derivatives (See U.S. Pat. No. 5,112,993).

Other methods comprise the step-growth polymerization from phosphonate, carboxylic, phosphate, sulfinate, sulfate and sulfonate functionals compounds. High density polyphosphonates such as Briquest, marketed by Rhodia, are particularly useful.

The polymers of the invention also include ion exchange resins synthesized from naturally occurring polymers, such as saccharide polymers and semi-synthetic polymers, optionally functionalized to create ion exchange sites on the backbone or on the pendant residues. Examples of polysaccharides of interest include materials from vegetal or animal origins, such as cellulosic materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan. Most preferred are polymers that do not degrade under the physiological conditions of the gastrointestinal tract and remain non-absorbed, such as carboxymethylcellulose, chitosan, and sulfoethylcellulose.

The potassium binding polymer can be encased in a dialysis bag, paper bag, microporous matrix, polymer gel, hollow fibers, vesicles, capsules, tablet, or a film.

The polymers can be formed by polymerization processes using either homogeneous or heterogeneous mode: in the former case a crosslinked gel is obtained by reacting the soluble polymer chains with a crosslinker, forming a bulk gel which is either extruded and micronized, or comminuted to smaller sized particles. In the former case, the particles are obtained by emulsification or dispersion of a soluble polymer precursor, and subsequently crosslinked. In another method, the particles are prepared by polymerization of a monomer in an emulsion, suspension, miniemulsion or dispersion process. The continuous phase is either an aqueous vehicle or an organic solvent. When a suspension process is used, any suitable type of variants is possible, including methods such as "templated polymerization," "multistage seeded suspension," all of which yielding mostly monodisperse particles. In one particular embodiment, the beads are formed using a "jetting" process (see U.S. Pat. No. 4,427,794), whereby a "tube of liquid containing a monomer plus initiator mixture is forced through a vibrating nozzle into a continuous phase. The nozzles can be arranged in spinning turret so as to force the liquid under centrifugal force.

In some embodiments wherein the potassium binding polymer is used without a shell, the potassium binding polymer is not kayexalate, sodium polystyrene sulfonate, or an ammonium form of polystyrene sulfonate.

In some embodiments, crown ethers and crown-ether like molecules are used as potassium binding polymers. Crown ethers show selectivity for certain alkali metals over others, based on the hole-size and the size of the metal ion. See Tables 2, 3 and 4 and Pedersen, C. J. 1987. Charles J. Pederson—Nobel Lecture. The discovery of crown ethers. In Nobel Lectures, Chemistry 1981-1990. T. Frangsmyr, editor. World Scientific Publishing Co., Singapore.

In yet another embodiment, crown ethers are used as shell materials to decrease the passage of sodium, magnesium, calcium and other interfering molecules to the core and as a result, increase the in vivo binding capacity of a core polymer.

TABLE 2

Diameters of holes in Sample Crown Ethers, in Angstrom units

| Macrocyclic Polyethers | Diameters |
|---|---|
| All 14-crown-4 | 1.2-1.5 |
| All 15-crown-5 | 1.7-2.2 |
| All 18-crown-6 | 2.6-3.2 |
| All 21-crown-7 | 3.4-4.3 |

TABLE 3

Complexable cations and their diameters in Angstrom units

| Group I | | Group II | | Group III | | Group IV | |
|---|---|---|---|---|---|---|---|
| Li | 1.36 | | | | | | |
| Na | 1.94 | | | | | | |
| K | 2.66 | Ca | 1.98 | | | | |

TABLE 3-continued

Complexable cations and their diameters in Angstrom units

| Group I | | Group II | | Group III | | Group IV | |
|---|---|---|---|---|---|---|---|
| Cu(I) | 1.92 | Zn | 1.48 | | | | |
| Rb | 2.94 | Sr | 2.26 | | | | |
| Ag | 2.52 | Cd | 1.94 | | | | |
| Cs | 3.34 | Ba | 2.68 | La | 2.30 | | |
| Au(I) | 2.88 | Hg(II) | 2.20 | Ti(I) | 2.80 | Pb(II) | 2.40 |
| Fr | 3.52 | Ra | 2.80 | | | | |
| $NH_4$ | 2.86 | | | | | | |

TABLE 4

Relative binding of sample alkali metal ions by sample crown ethers

| Polyether | $Li^+$ | $Na^+$ | $K^+$ | $Cs^+$ |
|---|---|---|---|---|
| Dicyclohexyl-14-crown-4 | 1.1 | 0 | 0 | 0 |
| Cyclohexyl-15-crown-5 | 1.6 | 19.7 | 8.7 | 4.0 |
| Dibenzo-18-crown-6 | 0 | 1.6 | 25.2 | 5.8 |
| Dicyclohexyl-18-crown-6 | 3.3 | 25.6 | 77.8 | 44.2 |
| Dicyclohexyl-21-crown-7 | 3.1 | 22.6 | 51.3 | 49.7 |
| Dicyclohexyl-24-crown-8 | 2.9 | 8.9 | 20.1 | 18.1 |

The potassium binding polymers typically include cationic counterions. The cations can be metallic, non-metallic, or a combination thereof. Examples of metallic ions include, but are not limited to, $Ca^{2+}$-form, $H^+$-form, $NH_4^+$-form, $Na^+$-form, or a combination thereof. Examples of non-metallic ions include, but are not limited to, alkylammonium, hydroxyalkylammonium, choline, taurine, carnitine, guanidine, creatine, adenine, and aminoacids or derivatives thereof.

In preferred embodiments, the potassium binding polymers described herein have a decreased tendency to cause side-effects such as hypernatremia and acidosis due to the release of detrimental ions. The term "detrimental ions" is used herein to refer to ions that are not desired to be released into the body by the compositions described herein during their period of use. Typically, the detrimental ions for a composition depend on the condition being treated, the chemical properties, and/or binding properties of the composition. For example, the detrimental ion could be $H^+$ which can cause acidosis or $Na^+$ which can cause hypernatremia. Preferably the ratio of potassium bound to detrimental cations introduced is 1: about 2.5 to about 4.

Core-Shell Compositions

In one aspect of the invention, a core-shell composition is used for the removal of potassium. Typically in the core-shell compositions, the core comprises a potassium-binding, preferably the polymer being capable of binding potassium with a high binding capacity. The various potassium-binding polymers described herein can be used as the core component of the core-shell compositions. In some embodiments, the shell modulates the entry of competing solutes such as magnesium and calcium across the shell to the core component. In one embodiment, the permeability of the membrane to divalent cations is diminished by decreasing the porosity to large hydrated cations such as alkaline-earth metals ions, and by incorporating positive charges that create electrostatic repulsion with said multivalent cations. It is preferred that the shell of the core-shell composition is essentially not disintegrated during the period of residence and passage through the gastrointestinal tract.

The term "competing solute" as used herein means solutes that compete with potassium for binding to a core component, but that are not desired to be contacted and/or bound to the core component. Typically, the competing solute for a core-shell composition depends on the binding characteristics of the core and/or the permeability characteristics of the shell component. A competing solute can be prevented from contacting and/or binding to a core-shell particle due to the preferential binding characteristics of the core component and/or the decreased permeability of the shell component for the competing solute from the external environment. Typically, the competing solute has a lower permeability from the external environment across the shell compared to that of potassium ions. Examples of competing solutes include, but are not limited to, $Mg^{++}$, $Ca^{++}$, and protonated amines.

In some embodiments, the shell is permeable to both mono- and di-valent cations. In some of the embodiments in which the shell is permeable to both mono- and di-valent cations, the core binds preferably mono-valent cations, preferably potassium, due to the binding characteristics of the core. In other embodiments, the shell exhibits preferred permeability to potassium ions.

It is particularly preferred that the core-shell compositions and the potassium binding polymeric compositions described herein bind potassium in the parts of the gastro-intestinal (GI) tract which have a relatively high concentration of potassium, such as in the colon. This bound potassium is then preferred to remain bound to the compositions and be excreted out of the body.

In one embodiment, the shell material protects the core component from the external GI environment. The shell material in some embodiments protects the acid groups of the core polymer and prevents their exposure to the GI environment. In one embodiment, the core component is protected with a shell component comprising of an enteric coating. Suitable examples of enteric coatings are described in the art. For example, see Remington: The Science and Practice of Pharmacy by A. R. Gennaro (Editor), 20$^{th}$ Edition, 2000.

In another embodiment the shell material is engineered to impose a lower permeability to higher valency cations. The permeability of the shell to alkaline-earth cations is altered by changing the average pore size, charge density and hydrophobicity of the membrane. $Mg^{++}$ and $Ca^{++}$ hydrated ions have a large size compared with monovalent cations such as $K^+$ and $Na^+$ as indicated below in Table 5 (Nightingale E. R., J. Phys. Chem., 63, (1959), 1381-89).

TABLE 5

| Metal ions | Hydrated radii (angstroms) |
| --- | --- |
| $K^+$ | 3.31 |
| $NH_4^+$ | 3.31 |
| $Na^+$ | 3.58 |
| $Mg^{++}$ | 4.28 |
| $Ca^{2+}$ | 4.12 |

Methods to reduced permeabilities to divalent cations are known from previous studies on cation-exchange membranes for electrodialysis (e.g. Sata et al, J. Membrane Science, 206 (2002), 31-60). Such methods are usually based on pore size exclusion and electrostatic interaction and combination thereof.

Accordingly, in some embodiments, several characteristics of the shell component are tuned so that a permeation difference is established. For example, when the mesh size of the shell material is in the same size range as the solute dimensions, the random walk of a bulkier divalent cation through the shell component is significantly slowed down. For example, experimental studies (Krajewska, B., Reactive and Functional polymers 47, 2001, 37-47) report permeation coefficients in cellulose ester or crosslinked chitosan gel membranes for both ionic and non-ionic solutes shows slowing down of bulkier solutes when mesh size nears solute dimensions. The polymer volume fraction in the swollen resin is a good indicator of the mesh size within the composition; theoretical studies have shown, for example, that mesh size usually scales with $\phi^{-3/4}$, $\phi$ being the polymer volume fraction in the shell component when swollen in a solution. The membrane swelling ratio depends on the hydrophobicity, crosslinking density, charge density, and solvent ionic strength.

For instance polypyrrole layered on the cation exchange materials by in-situ polymerization of pyrrole, is shown to induce permselectivity by creating a very tightly porous membrane that hinders large divalent cation diffusion relatively to monovalent cations.

Alternatively a thin monolayer of a cationic polyelectrolyte is physically adsorbed to create a strong electrical field that repel highly charged cations such as $Mg^{++}$ and $Ca^{++}$. Suitable cationic polyelectrolytes include, but are not limited to, copolymers with a repeat unit selected from vinylamine, ethyleneimine, propyleneimine, allylamine, vinylpyridines, alkyaminoalkyl(meth)acrylates, alkyaminoalkyl(meth)acrylamides, aminomethylstyrene, chitosan, adducts of aliphatic amine or aromatic amine with electrophiles such as epichlorhydrine, alkylhalides or epoxydes, and wherein the amine is optionally a quarternized form. Adducts of aliphatic amine or aromatic amine with alkyldihalides are also referred to as ionenes. The polymeric permselectivity can also be controlled by pH, whereupon the polymer charge density and swelling ratio varies with the rate of (de)protonation.

pH-controlled binding selectivity is an important lever when the counter-ion initially loaded in the polymer has to be displaced and eventually replaced by potassium. If the polymer is first conditioned with $Ca^{++}$, a divalent cation with a high binding constant to carboxylic or sulfonic groups, one can take advantage of the acidic environment encountered in the stomach to protonate the binding sites of the polymer so as to displace the initially loaded counter-ion (i.e. Ca). In that context, it is advantageous to design polymers with ion exchange properties varying with the local pH, more preferably polymers with a low binding capacity at gastric pH and a high capacity at pH greater than about 5.5. In one preferred embodiment, the polymers of the invention have a fraction of capacity available at pH lower than about 3, of about 0-10% of the full capacity (i.e. measure at pH about 12), and greater than about 50% at pH greater than about 4.

Methods for determining permeability coefficients are known. For example, see, W. Jost, *Diffusion in Solids, Liquids and Gases*, Acad. Press, New-York, 1960). For example, the ion permeability coefficient in a shell polymer can be measured by casting the polymer as a membrane over a solid porous material, subsequently contacted with a physiological solution (donor) containing the ions of interest, and measuring steady state permeation rates of said ions, across the membrane in the acceptor solution. Membrane characteristics can then be optimized to achieve the best cooperation in terms of selectivity and permeation rate kinetics. Structural characteristics of the membrane can be varied by modifying, for example, the polymer volume fraction (in the swollen membrane), the chemical nature of the polymer(s) and its properties (hydrophobicity, crosslinking density, charge density), the polymer blend composition (if more than one polymer is used), the formulation with additives such as wetting agents, plasticizers, and/or the manufacturing process.

The permselective membranes of the invention are optimized by studying their permselectivity profile as a function of polymer compositions and physical characteristics. Permselectivity is preferably measured in conditions close to those prevailing in the milieu of use (e.g. colon). In a typical experiment, the donor solution is a synthetic fluid with an ionic composition, osmolality, and pH mimicking the colonic fluid, or alternatively, an animal fluid collected through ileostomy or coleostomy. In another embodiment, the membrane is sequentially contacted with fluids that model the conditions found in the different parts of the GI tract, i.e. stomach, duodenum, jejunum, and ileum. In yet another embodiment, the shell is deposited on a cation exchange resin bead under the proton form by microencapsulation method and contacted with a sodium hydroxide aqueous solution. By monitoring pH or conductivity the rate of permeation of NaOH across the membrane is then computed. In another embodiment the resin is preloaded with lithium cations and the release of lithium and absorption of sodium, potassium, magnesium, calcium and ammonium are monitored by ion chromatography. In a preferred embodiment, the permeability ratio of potassium and divalent cations such as $Mg^{++}$ and $Ca^{++}$, measured in the aforementioned conditions is comprised between about 1:0.5 to about 1:0.0001, preferably between about 1:0.2 and about 1:0.01.

In another embodiment, the shell of a core-shell composition displays a permeability selectivity by passive absorption while passing through the upper GI tract. Many components present in the GI tract including components of the diet, metabolites, secretion, etc. are susceptible to adsorb onto and within the shell in a quasi-irreversible manner and can strongly modify the permeability pattern of the shell. The vast majority of these soluble materials are negatively charged and show various levels of hydrophobicity. Some of those species have a typical amphiphilic character, such as fatty acids, phospholipids, bile salts and can behave as surfactants. Surfactants can adsorb non-specifically to surfaces through hydrophobic interactions, ionic interaction and combinations thereof. In this embodiment, this phenomenon is used to change the permeability of the polymeric composition upon the course of binding potassium ions. In one embodiment fatty acids can be used to modify the permeability of the shell and in another embodiment bile acids can be used. Fatty acids and bile acids both form aggregates (micelles or vesicles) and can also form insoluble complexes when mixed with positively charged polymers (see e.g. Kaneko et al, *Macromolecular Rapid Communications* (2003), 24(13), 789-792). Both fatty acids and bile acids exhibit similarities with synthetic anionic surfactants and numerous studies report the formation of insoluble complexes between anionic surfactants and cationically charged polymers (e.g. Chen, L. et al, *Macromolecules* (1998), 31(3), 787-794). In this embodiment, the shell material is selected from copolymers containing both hydrophobic and cationic groups, so that the shell forms a tight complex with anionically charged hydrophobes typically found in the GI tract, such as bile acids, fatty acids, bilirubin and related compounds. Suitable compositions also include polymeric materials described as bile acids sequestering agents, such as those reported in U.S. Pat. Nos. 5,607,669; 6,294,163; and 5,374,422; Figuly et al, *Macromolecules*, 1997, 30, 6174-6184. The formation of the complex induces a shell membrane collapse which in turn can lower the diffusion of bulky divalent cations, while leaving the permeation of potassium unchanged.

In yet another embodiment, the permeability of the shell of a core-shell composition is modulated by enzymatic activity in the gastro-intestinal tract. There are a number of secreted enzymes produced by common colonic microflora. For example *Bacteroides, Prevotella, Porphyromonas*, and *Fusobacterium* produce a variety of secreted enzymes including collagenase, neuraminidase, deoxyribonuclease [DNase], heparinase, and proteinases. In this embodiment the shell comprises a hydrophobic backbone with pendant hydrophilic entities that are cleaved off via an enzymatic reaction in the gut. As the enzymatic reaction proceeds, the polymer membrane becomes more and more hydrophobic, and turns from a high swollen state, high permeability rate material to a fully collapsed low hydration membrane with minimal permeability to bulky hydrated cations such as $Mg^{++}$ and $Ca^{++}$. Hydrophilic entities can be chosen from natural substrates of enzymes commonly secreted in the GI tract. Such entities include amino acids, peptides, carbohydrates, esters, phosphate esters, oxyphosphate monoesters, O- and S-phosphorothioates, phosphoramidates, thiophosphate, azo groups and the like. Examples of enteric enzymes susceptible to chemically alter the shell polymer include, but are not limited to, lipases, phospholipases, carboxylesterase, glycosidases, azoreductases, phosphatases, amidases and proteases. The shell can be permeable to potassium ions until it enters the proximal colon and then the enzymes present in the proximal colon can react chemically with the shell to reduce its permeability to the divalent cations.

In some embodiments, the shell thickness can be between about 0.002 micron to about 50 micron, preferably about 0.005 micron to about 20 microns. Preferably the shell thickness is more than about 0.5 micron, more preferred is more than about 2 micron, even more preferred is more than about 5 micron. Preferably the shell thickness is less than about 30 micron, more preferred is less than about 20 micron, even more preferred is less than about 10 micron, and most preferred is less than about 5 micron.

The size of the core-shell particles typically range from about 200 nm to about 2 mm, preferably being about 100 microns. Preferably the size of the core-shell particles are more than about 1 microns, more preferred is more than about 10 microns, even more preferred is more than about 20 microns, and most preferred is more than about 40 microns. Preferably the size of the core-shell particles are less than about 250 microns, more preferred is less than about 150 microns, even more preferred is less than about 100 microns, and most preferred is less than about 50 microns.

Synthesis of Core-shell Particles

In preferred embodiments, the shell is uniformly coated on the core material, preferably without pinholes or macroporosity and is light weight relative to the core material (for example, up to about 20 wt-%). The shell can be anchored to the core and preferably resistant enough to sustain the mechanical constraint such as swelling and compression encountered during tablet formulation.

The shell can be formed by chemical or non-chemical processes. Non-chemical processes include spray coating, fluid bed coating, solvent coacervation in organic solvent or supercritical $CO_2$, solvent evaporation, spray drying, spinning disc coating, extrusion (annular jet) or layer by layer formation. Examples of chemical processes include interfacial polymerization, grafting from, grafting unto, and core-shell polymerization.

In fluid bed coating, typically the core beads are kept in a recirculating fluidized bed (Wurster type) and sprayed with a coating solution or suspension. The coating polymer can be used as a solution in ethylacetate, ketones, or other suitable solvents or as latex. Conditions are typically optimized so as to form a tight and homogeneous membrane layer, and insure that no cracks are formed upon swelling when the particles are contacted with the aqueous vehicle. It is preferred that the membrane polymer can yield to the volume expansion and elongates so as to accommodate the dimension change. Polymer membranes have an elongation at break greater than 10%, preferably greater than 30%. Examples of this approach are reported in Ichekawa H. et al, International Journal of Pharmaceuticals, 216(2001), 67-76.

Solvent coacervation is described in the art. For example, see Leach, K. et al., J. Microencapsulation, 1999, 16(2), 153-167. In this process, typically two polymers, core polymer and shell polymer are dissolved in a solvent which is further emulsified as droplets in an aqueous phase. The droplet interior is typically a homogeneous binary polymer solution. The solvent is then slowly driven off by careful distillation. The polymer solution in each droplet undergoes a phase separation as the volume fraction of polymer increases. One of the polymer migrates to the water/droplet interface and forms a more-or less perfect core-shell particle (or double-walled microsphere).

A variant of this approach is when core particles are first dispersed in a polymer solution containing both a solvent and a non-solvent for that polymer. The solvent is distilled off until all the polymer precipitates as a coated layer on the core-particle.

Supercritical $CO_2$ coating is described in the art. For example, see Benoit J. P. et al, J. Microencapsulation, 2003, 20(1)87-128. This approach is somewhat a variant of the solvent coacervation. First the shell coating material is dissolved in the supercritical $CO_2$, and then the active is dispersed in that fluid in super-critical conditions. The reactor is cooled down to liquid $CO_2$ conditions wherein the shell material is no longer soluble and precipitates on the core beads. The process is exemplified with shell materials selected from small molecules such as waxes and parafins. The core-shell material is recovered as a powder.

The spinning disc coating technique is based on forming a suspension of the core particles in the coating, then using a rotating disc to remove the excess coating liquid in the form of small droplets, while a residual coating remains around the core-particles. See U.S. Pat. No. 4,675,140.

In the layer by layer process, a charged core material is contacted with a polyelectrolyte of opposite charge and a polymer complex is formed. This step is repeated until a multilayer is deposited on the core surface. Further crosslinking of the layers are optional.

Interfacial polymerization consists of dispersing the core material containing one reacting monomer in a continuous phase containing a co-reacting monomer. A polymerization reaction takes place at the core interface creating a shell polymer. The core can be hydrophilic or hydrophobic. Typical monomer used for that purpose can include diacylchlorides/diamines, diisocyanates/diamines, diisocyanates/diols, diacylchlorides/diols and bischloroformate and diamines or diols. Trifunctional monomers can also be used to control the degree of porosity and toughness of the membranes.

In yet another embodiment, the shell is formed by contacting the ion exchange material with a polymer dispersion of opposite charge (i.e. the core material is typically charged negatively and the shell positively), and filter the bead particles and anneal them in a fluidized bed at a temperature higher than the transition temperature (or softening point) of the shell polymer. In this embodiment the polymer dispersion is a latex or a polymer colloidal dispersion of particle size in the micron to sub-micron range.

In one further embodiment, the shell material comprises treating the acid containing core material with acid reactive monomer or polymer. Preferably the acid reactive material is a polymer and more preferably a polyamine: for instance a carboxylated core polymer is treated with polyethyleneimine at high temperature in an organic solvent to create amide bonds between the COOH groups and the NH and $NH_2$ groups. It can also be useful to activate the acid functions to facilitate the amide bond formation, e.g. by treating COOH or $SO_3H$ groups with thionylchloride or chlorosulfonic acid to convert said groups into their acid chloride forms. See Sata et al., Die Angewandte Makromolekulare Chemie 171, (1989) 101-117 (Nr2794).

The process of "grafting from" involves an active site capable of initiating polymerization on the core surface and polymer chains are grown from the surface in monolayers. Living polymerization methods such as nitroxide-mediated living polymerizations, ATRP, RAFT, ROMP are most suitable, but non living polymerizations have also been applied.

In the process of "grafting onto" a small molecule (typically an electrophile, such as epoxy, isocyanate, anhydride, etc.) is brought in contact with the polymeric core material, said core carrying reactive species (typically nucleophile groups such as amine, alcohol, etc.). The thickness of the shell thus formed is controlled by the rate of diffusion of the shell small molecule precursor and the rate of reaction with the core. Slow-diffusing/highly reactive species tend to confine the reaction within a short distance from the core surface thus producing a thin shell. Whereas, fast-diffusing/slow reacting species tend to invade the entire core with no defined shell and form a gradient rather than a sharp shell to core boundary.

Core-shell polymerizations can be emulsion polymerization, suspension/mini-emulsion polymerization, or dispersion polymerization. All these processes employ free radical polymerizations. In emulsion polymerization, the polymerization takes place in aqueous medium with a surfactant, monomer with a low water solubility, and a water soluble free radical initiator. Polymer particles are formed by micellar or homogeneous nucleation or both. Core shell particles can be formed theoretically by feeding the core monomer first and the shell monomer second as long as the monomer is spontaneously consumed as it is fed ("starved regime"). The potassium binding core beads are preferably made from a water insoluble monomer (e.g. alkylester of a-fluoro-acrylic acid).

In suspension/mini-emulsion polymerization, the free radical initiator is soluble with the monomer. Monomer and initiator are pre-dissolved and then emulsified in droplet stabilized with either surfactant or amphiphilic polymers. This method allows one pre-formed polymer (e.g. the shell polymer) to be dissolved as well. When the reaction proceeds, the shell polymer and the core polymer phase separate to form the desired core-shell particles.

In dispersion polymerization, both the monomer and the initiator are soluble in the continuous phase (usually an organic solvent). A block copolymer is used as a steric stabilizer. The polymer particles are formed by homogenous nucleation and subsequent growth. Particle size are on the 1 to 10 microns range and mono-dispersed.

In a preferred process of dispersion, polymerization employs a refinement reported in Stover H. et al, Macromolecules, 1999, 32, 2838-2844, described thereafter: The shell monomer contains a large fraction of divinyl monomer, such as 1,4 divinylbenzene, while the core particles present some polymerizable double bond on their surface; the shell polymerization mechanism is based on the formation of short oligoradicals in the continuous phase, which are captured by the double bond present on the particle surface. The oligomers themselves contain non-reacted insaturation that replenish the surface in reactive double bonds. The net result is a formation of a crosslinked shell with a sharp boundary with the shell and the core material.

In one embodiment, a core-shell composition of the invention is synthesized by forming the cation exchange core in a conventional inverse suspension process using suitable monomers; decorating the particle surface with reactive double bonds by post-reacting with the acidic group present on the particle core; and dispersing in typical dispersion polymerization solvent such as acetonitrile (e.g. a non-solvent for the cation-exchange core polymer) and adding a polymerizing mixture of DVB or EGDMA with a functional monomer.

Methods of Treatments

The methods and compositions described herein are suitable for treatment of hyperkalemia caused by disease and/or use of certain drugs.

In some embodiments of the invention, the compositions and methods described herein are used in the treatment of hyperkalemia caused by decreased excretion of potassium, especially when intake is not reduced. A common cause of decreased renal potassium excretion is renal failure (especially with decreased glomerular filtration rate), often coupled with the ingestion of drugs that interfere with potassium excretion, e.g., potassium-sparing diuretics, angiotensin-converting enzyme inhibitors (ACEIs), non-steroidal anti-inflammatory drugs, heparin, or trimethoprim. Impaired responsiveness of the distal tubule to aldosterone, for example in type IV renal tubular acidosis observed with diabetes mellitus as well as sickle cell disease and/or chronic partial urinary tract obstruction is another cause of reduced potassium secretion. Secretion is also inhibited in diffuse adrenocortical insufficiency or Addison's disease and selective hypoaldosteronism. Hyperkalemia is common when diabetics develop hypoteninemic hypoaldosteronism or renal insufficiency (Mandal, A. K. 1997. Hypokalemia and hyperkalemia. Med Clin North Am. 81:611-39).

In certain preferred embodiments, the potassium binding polymers described herein are administered chronically. Typically, such chronic treatments will enable patients to continue using drugs that cause hyperkalemia, such as potassium-sparing diuretics, ACEI's, non-steroidal anti-inflammatory drugs, heparin, or trimethoprim. Also, use of the polymeric compositions described herein will enable certain patient populations, who were unable to use hyperkalemia causing drugs, to use such drugs.

In certain chronic use situations, the preferred potassium binding polymers used are those that are capable of removing less than about 5 mmol of potassium per day or in the range of about 5-about 10 mmol of potassium per day. In acute conditions, it is preferred that the potassium binding polymers used are capable of removing about 15-about 60 mmol of potassium per day.

In certain other embodiments, the compositions and methods described herein are used in the treatment of hyperkalemia caused by a shift from intracellular to extracellular space. Infection or trauma resulting in cell disruption, especially rhabdomyolysis or lysis of muscle cells (a major potassium store), and tumor lysis can result in acute hyperkalemia. More often, mild-to-moderate impairment of intracellular shifting of potassium occurs with diabetic ketoacidosis, acute acidosis, infusion of argentine or lysine chloride for the treatment of metabolic alkalosis, or infusion of hypertonic solutions such as 50% dextrose or mannitol. β-receptor blocking drugs can cause hyperkalemia by inhibiting the effect of epinephrine.

In certain other embodiments, the compositions and methods described herein are used in the treatment of hyperkalemia caused by excessive intake of potassium. Excessive potassium intake alone is an uncommon cause of hyperkalemia. Most often, hyperkalemia is caused by indiscriminate potassium consumption in a patient with impaired mechanisms for the intracellular shift of potassium or renal potassium excretion. For example, sudden death among dialyzed patients who are noncompliant in diet can be attributed to hyperkalemia.

In the present invention, the potassium-binding polymers and the core-shell compositions can be co-administered with other active pharmaceutical agents. This co-administration can include simultaneous administration of the two agents in the same dosage form, simultaneous administration in separate dosage forms, and separate administration. For example, for the treatment of hyperkalemia, the potassium-binding polymers and the core-shell compositions can be co-administered with drugs that cause the hyperkalemia, such as potassium-sparing diuretics, angiotensin-convening enzyme inhibitors, non-steroidal anti-inflammatory drugs, heparin, or trimethoprim. The drug being co-administered can be formulated together in the same dosage form and administered simultaneously. Alternatively, they can be simultaneously administered, wherein both the agents are present in separate formulations. In another alternative, the drugs are administered separately. In the separate administration protocol, the drugs may be administered a few minutes apart, or a few hours apart, or a few days apart.

The term "treating" as used herein includes achieving a therapeutic benefit and/or a prophylactic benefit. By therapeutic benefit is meant eradication, amelioration, or prevention of the underlying disorder being treated. For example, in a hyperkalemia patient, therapeutic benefit includes eradication or amelioration of the underlying hyperkalemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of a potassium-binding polymer to a patient suffering from hyperkalemia provides therapeutic benefit not only when the patient's serum potassium level is decreased, but also when an improvement is observed in the patient with respect to other disorders that accompany hyperpkalemia like renal failure. For prophylactic benefit, the potassium-binding polymers may be administered to a patient at risk of developing hyperpkalemia or to a patient reporting one or more of the physiological symptoms of hyperpkalemia, even though a diagnosis of hyperpkalemia may not have been made.

The pharmaceutical compositions of the present invention include compositions wherein the potassium binding polymers are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein.

The effective amount for use in humans can be determined from animal models. For example, a dose for humans can be formulated to achieve gastrointestinal concentrations that have been found to be effective in animals.

The dosages of the potassium binding polymers in animals will depend on the disease being, treated, the route of administration, and the physical characteristics of the patient being treated. Dosage levels of the potassium binding polymers for therapeutic and/or prophylactic uses can be from about about 0.5 gm/day to about 30 gm/day. It is preferred that these polymers are administered along with meals. The compositions may be administered one time a day, two times a day, or three times a day. Most preferred dose is about 15 gm/day or less. A preferred dose range is about 5 gm/day to about 20 gm/day, more preferred is about 5 gm/day to about 15 gm/day, even more preferred is about 10 gm/day to about 20 gm/day, and most preferred is about 10 gm/day to about 15 gm/day.

In some embodiments, the amount of potassium bound by the core-shell compositions is greater than the amount if the core component, i.e., potassium binding polymer is used in the absence of the shell. Hence, the dosage of the core component in some embodiments is lower when used in combination with a shell compared to when the core is used without the shell. Hence, in some embodiments of the core-shell pharmaceutical compositions, the amount of core component present in the core-shell pharmaceutical composition is less than the amount that is administered to an animal in the absence of the shell component.

The compositions described herein can be used as food products and/or food additives. They can be added to foods prior to consumption or while packaging to decrease levels of potassium. The compositions can also be used in fodder for animals to lower $K^+$ levels, which is for example desirable for example in fodders for pigs and poultry to lower the water secretion.

Formulations and Routes of Administration

The polymeric compositions and core-shell compositions described herein or pharmaceutically acceptable salts thereof, can be delivered to the patient using a wide variety of routes or modes of administration. The most preferred routes for administration are oral, intestinal, or rectal.

If necessary, the polymers and core-shell compositions may be administered in combination with other therapeutic agents. The choice of therapeutic agents that can be co-administered with the compounds of the invention will depend, in part, on the condition being treated.

The polymers (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present invention may be formulated in conventional manner using one or more physiologically acceptable carriers compromising excipients and auxiliaries which facilitate processing of the active compounds into preparations which can be used pharmaceutically. Proper formulation is dependent upon the route of administration chosen.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions, wafers, and the like, for oral ingestion by a patient to be treated. In one embodiment, the oral formulation does not have an enteric coating. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, mehtyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For administration orally, the compounds may be formulated as a sustained release preparation. Numerous techniques for formulating sustained release preparations are known in the art.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

EXAMPLES

Example 1

Preparation of Polymers with High Binding Capacity

Materials:

All chemicals were purchased from commercial sources and used as received. All reactions were carried out under nitrogen. Chemical structures and used abbreviations are given below in Tables 6 and 7.

TABLE 6

Monomer Abbreviations and Structures

| Abbreviation | Chemical name | Structure | Molecular Weight | CAS # |
|---|---|---|---|---|
| Na-VSA | vinylsulfonic acid sodium salt | 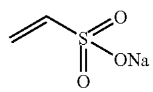 | 130.1 | 3039-83-6 |
| FAA | 2-fluoroacrylic acid or α-fluoroacrylic acid or 2-fluoropropenoic acid | 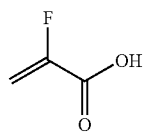 | 90.05 | 430-99-9 |
| VPA | vinylphosphonic acid | 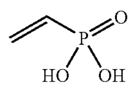 | 108.03 | 1746-03-8 |

TABLE 7

Crosslinker Abbreviations and Structures

| Abbreviation | Chemical name | Structure | Molecular Weight | CAS# |
|---|---|---|---|---|
| X-V-1 | ethylenebisacrylamide | 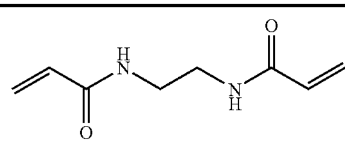 | 168.2 | 2956-58-3 |
| X-V-2 | | 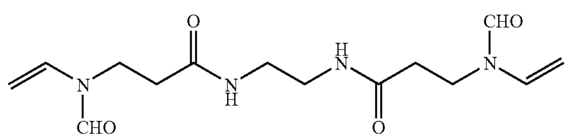 | 310.36 | |
| X-V-3 | | 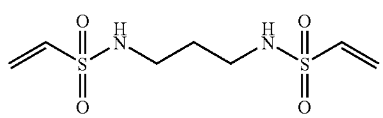 | 254.33 | |
| X-V-4 | N,N'-bis(vinylsulfonylacetyl) ethylene diamine | 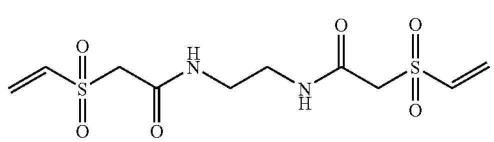 | 324.38 | 66710-66-5 |
| X-V-5 | 1,3-bis(vinylsulfonyl) 2-propanol | 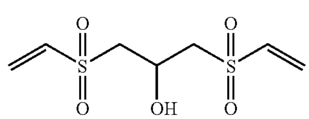 | 240.3 | 67006-32-0 |
| X-V-6 | vinylsulfone | 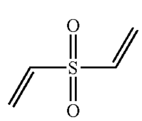 | 118.15 | 77-77-0 |
| X-V-7 | N,N'-methylenebisacrylamide | 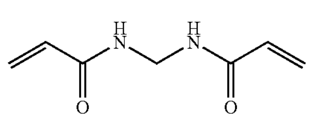 | 154.17 | 110-26-9 |
| ECH | epichlorohydrin | 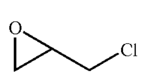 | 92.52 | |

Initiators: VA-044: 2,2'-azobis[2-(2-imidazolin-2-yl)propane]dihydrochloride; $K_2S_2O_8$, potassium persulfate General Procedure for Gel Preparation from FAA:

To a 15-ml test tube were charged FAA, X-V-1, and water, followed by a magnetic stirbar. The mixture was stirred at 45° C. for 20 minutes and VA-044 (100 mg/ml solution in water) was added. The solution gelled and was kept at 45° C. for 4 hours, then cooled to room temperature.

The gel was transferred to a 50-ml polypropylene tube and water was added to a total volume of 30 ml. The gel was crushed with a spatula, and further milled with an Ultra-Turrax. The tube was capped and centrifuged at 3000 rpm for 30 minutes and the supernatant solution was decanted off. To the gel was added 1.0M HCl to a total volume of 45 ml and tube was capped and tumbled for 30 minutes. The tube was centrifuged at 3000 rpm for 30 minutes and supernatant solution was decanted off. The same tumbling-centrifuging procedure was repeated once with 1.0M HCl and three times with nanopure water. The gel was freeze-dried for three days. The reaction solution composition and gel yield are displayed in Table 8.

TABLE 8

Synthesis of FAA gels

| | Reaction solution composition | | | |
|---|---|---|---|---|
| Sample # | FAA (mg) | X-V-1 (mg) | Water (mL) | VA-044 (mL) | Yield (mg) |
| 628A | 757 | 19 | 0.757 | 0.038 | 740 |
| 628B | 737 | 37 | 0.737 | 0.037 | 760 |
| 628C | 730 | 73 | 0.730 | 0.037 | 760 |
| 628D | 691 | 138 | 0.691 | 0.035 | 780 |

General Procedure for Gel Preparation from Na VSA:

Commercially available NaVSA was converted into acid form and purified by vacuum distillation according to a method described by Breslow et al (*J. Am. Chem. Soc.*, 1954, 76, 6399-6401). The pure acid was then dissolved in water and neutralized with NaOH solution carefully at 0° C. The colorless salt solution was concentrated by vacuum distillation to a concentration of 56 wt. %.

To a 15-ml test tube were charged NaVSA solution, crosslinker, and a magnetic stirbar and the mixture was stirred at 45° C. for 20 minutes. VA-044 (50 mg/mL solution in water) or $K_2S_2O_8$ (50 mg/mL solution in water) was added. The solution was stirred at 45° C. (if VA-044 used) or 50° C. (if $K_2S_2O_8$ used) for 16 hours, then cooled to room temperature. The gel was purified according to the same procedure as used for FAA gel. The reaction solution composition and gel yield were displayed in Table 9.

TABLE 9

Synthesis of NaVSA gels

| | Reaction solution composition | | | | | |
|---|---|---|---|---|---|---|
| Sample # | NaVSA (mL) | X-V-1 (mg) | X-V-5 (mg) | VA-044 (mL) | $K_2S_2O_8$ (mL) | Yield (mg) |
| 100851A1 | 1.493 | 28 | 0 | 0.056 | 0 | 0 |
| 100851A2 | 1.493 | 56 | 0 | 0.056 | 0 | 400 |
| 100851A3 | 1.493 | 112 | 0 | 0.056 | 0 | 740 |
| 100851A4 | 1.493 | 225 | 0 | 0.056 | 0 | 590 |
| 100851B1 | 1.493 | 0 | 28 | 0.056 | 0 | 550 |
| 100851B2 | 1.493 | 0 | 56 | 0.056 | 0 | 830 |
| 100851B3 | 1.493 | 0 | 112 | 0.056 | 0 | 890 |
| 100851B4 | 1.493 | 0 | 225 | 0.056 | 0 | 800 |
| 100851C1 | 1.493 | 28 | 0 | 0 | 0.056 | 0 |
| 100851C2 | 1.493 | 56 | 0 | 0 | 0.056 | 420 |
| 100851C3 | 1.493 | 112 | 0 | 0 | 0.056 | 760 |
| 100851C4 | 1.493 | 225 | 0 | 0 | 0.056 | 730 |
| 100851D1 | 1.493 | 0 | 28 | 0 | 0.056 | 390 |
| 100851D2 | 1.493 | 0 | 56 | 0 | 0.056 | 540 |
| 100851D3 | 1.493 | 0 | 112 | 0 | 0.056 | 890 |
| 100851D4 | 1.493 | 0 | 225 | 0 | 0.056 | 720 |

General Procedure for Gel Preparation from Copolymerization of NaVSA and FAA:

To a 15-ml test tube were charged FAA and NaVSA solution, followed by a magnetic stirbar. The mixture was stirred at room temperature for 10 minutes and all FAA dissolved. X-V-1 was added and mixture was stirred at room temperature for 10 minutes, then at 45° C. for 20 minutes. VA-044 (100 mg/ml solution in water) was added and the solution was stirred at 45° C. for 3 hours, then cooled to room temperature. The gel was purified according to the same procedure as used for FAA gel. The reaction solution composition and gel yield were displayed in Table 10.

TABLE 10

Synthesis of NaVSA/FAA gels

| | Reaction solution composition | | | |
|---|---|---|---|---|
| Sample # | FAA (mg) | NaVSA (mL) | X-V-1 (mg) | Va-044 (mL) | Yield (mg) |
| 101028A1 | 0 | 1.328 | 100 | 0.100 | 600 |
| 101028A2 | 100 | 1.195 | 100 | 0.100 | 630 |
| 101028A3 | 200 | 1.062 | 100 | 0.100 | 720 |
| 101028A4 | 300 | 0.930 | 100 | 0.100 | 780 |
| 101028A5 | 400 | 0.797 | 100 | 0.100 | 730 |
| 101028A6 | 500 | 0.664 | 100 | 0.100 | 700 |

General Procedure for Gel Preparation from Copolymerization of AA and FAA:

To a 15-ml test tube containing a magnetic stirbar, were charged FAA, X-V-1 and water, and the mixture was stirred until all solids dissolved. AA was added, followed by VA-044 (100 mg/ml solution in water). The mixture was stirred at 45° C. for 3 hours, then cooled to room temperature. The gel was purified according to the same procedure as used for FAA gel. The reaction solution composition and gel yield were displayed in Table 11.

TABLE 11

Synthesis of FAA/AA gels

| | Reaction solution composition | | | | |
|---|---|---|---|---|---|
| Sample # | FAA (mg) | AA (mL) | X-V-1 (mg) | Water (mL) | VA-044 (mL) | Yield (mg) |
| 100982A1 | 800 | 0 | 80 | 0.764 | 0.040 | 770 |
| 100982A2 | 720 | 0.076 | 80 | 0.764 | 0.040 | 700 |
| 100982A3 | 640 | 0.152 | 80 | 0.764 | 0.040 | 730 |

TABLE 11-continued

Synthesis of FAA/AA gels

Reaction solution composition

| Sample # | FAA (mg) | AA (mL) | X-V-1 (mg) | Water (mL) | VA-044 (mL) | Yield (mg) |
|---|---|---|---|---|---|---|
| 100982A4 | 560 | 0.228 | 80 | 0.764 | 0.040 | 740 |
| 100982A5 | 480 | 0.304 | 80 | 0.764 | 0.040 | 740 |
| 100982A6 | 400 | 0.380 | 80 | 0.764 | 0.040 | 730 |

General Procedure for Preparation of poly(vinylsulfamate) Gel:

Polyvinylamine hydrochloride (PVAm.HCl) was prepared according to a literature procedure by Badesso et al (in *Hydrophilic Polymers: Performance with Environmental acceptance*, P489-504). PVAm gel was prepared by the crosslinking reaction of PVAm.HCl with epichlorohydrin. The procedure was as follows: to a 100 ml of round bottom flask was charged 33 wt % PVAm.HCl aqueous solution (15 gm, 62.9 mmol), followed by 50 wt % NaOH solution (2.63 gm) to neutralize 50 mol % of PVAm.HCl. Epichlorohydrin (1.0 gm) was added and the mixture was stirred magnetically until stirring stopped due to gel formation. The gel was further cured at 65° C. for 12 hours and transferred to a 50-ml polypropylene tube, and then water was added to a total volume of 30 ml. The gel was crushed with a spatula, and further milled with an Ultra-Turrax. The gel was washed with 1 M HCl and nanopure water using the procedure described for FAA gel. Finally, PVAm gel was freeze dried for 3 days.

General Procedure for Preparing poly(vinylsulfamate) Gel:

To a 20 ml vial was added 0.5 gm of PVAm gel and 10 ml of solvent. The mixture was heated at 60° C. for 1 hour, then 0.5 gm of sulfur trioxide trimethylamine ($SO_3.N(CH_3)_3$) was added. Inorganic base, $Na_2CO_3$ or 2M NaOH solution, was added to the reaction mixture to maintain the pH above 9. The mixture was heated at 60° C. for a certain time. The mixture was centrifuged, and supernatant solution was decanted off. The gel was washed with nanopure water until pH reached 7, and freeze dried. The reaction conditions and the conversion of amine group to sulfamate group are shown in Table 12.

TABLE 12

Preparation of poly(vinylsulfamate) gel

| Sample # | Ratio of $(CH_3)_3 \cdot SO_3$ to $NH_2$ | Base | Reaction time (hours) | Solvent | Conversion (%) |
|---|---|---|---|---|---|
| 001 | 1:1 | None | 3 | Water | 22.4 |
| 002 | 1:1 | None | 10 | Water | 37.1 |
| 003 | 1:1 | None | 22 | Water | 40.8 |
| 008 | 1:1.5 | $(CH_3)_3N$ | 22 | $(CH_3)_3N$/water (20 vol %) | 65.5 |
| 010 | 1:1.5 | Pyridine | 22 | Pyridine/Water (20 wt %) | 4.84 |
| 013 | 1:1 | $Na_2CO_3$ | 22 | Water | 80.5 |
| 014 | 1:1.5 | $Na_2CO_3$ | 22 | Water | 86.1 |
| 015 | 1:1 | NaOH | 22 | Water | 72.5 |
| 016 | 1.5 | NaOH | 22 | water | 73.5 |

Example 2

Binding Capacity Screening Protocol

All experiments were performed in duplicate. Approximately 30 mg of each polymer was aliquoted in duplicate into 16×100 mm glass test tubes. Dowex 50 W and Amberlite CG-50 were included in each experiment as internal controls. The relevant test binding buffer (Buffer 1, Buffer 2 or Buffer 3 below) was added to a final resin concentration of 2.5 mg/ml. The test tubes were sealed using a Teflon membrane and incubated at room temperature, with constant end-over-end rotation, for at least one hour to allow the cations to achieve binding equilibrium with the polymers. The test tubes were then centrifuged at 500 g for thirty minutes to isolate the resins. A sample of the supernatant was taken and the equilibrium concentrations of potassium ($K^+_{eq}$) and sodium ($Na^+_{eq}$) were determined by Ion Chromatography (IC). By comparing $K^+_{eq}$ and $Na^+_{eq}$ with the concentration of potassium in Buffer 1, Buffer 2 or Buffer 3 in the absence of polymer ($K^{+start}$ and $Na^+_{start}$), the amount of cation (in mmoles cation/gram of polymer) was calculated. The ratio of sodium and potassium bound to the polymer was also calculated in this manner.

The capacity of each resin for Sodium and for Potassium was tested under some or all of the following conditions:
1. 75 mM NaOH, 75 mM KOH (pH not adjusted)
2. 50 mM Citric Acid, 75 mM KOH, 75 mM NaOH, pH 6.35 (with HCl)
3. 50 mM Citric Acid, 75 mM KOH, 75 mM NaOH, pH 3 (with HCl)

TABLE 13

Binding capacities of phosphonic, carboxylic, and sulfonic polymers

| Sample Name | Description | Total mmoles ($Na^+ + K^+$) bound/gm resin, pH 12.5 | $Na^+:K^+$ ratio at pH 12.5 | Total mmoles ($Na^+ + K^+$) bound/gm resin, pH 6.25 | $Na^+:K^+$ ratio at pH 6.25 | Total mmoles ($Na^+ + K^+$) bound/gm resin, pH 3 | $Na^+:K^+$ ratio at pH 3 |
|---|---|---|---|---|---|---|---|
| 616B3 | NaVSA + 20 wt. % X-V-1 | | | | | | |
| 624B | NaVSA + 5 wt. % X-V-2 | | | | | | |
| 624C | NaVSA + 10 wt. % X-V-2 | 6.91 | 0.76 | 6.35 | 0.78 | 6.43 | 0.76 |
| 624D | NaVSA + 20 wt. % X-V-2 | 6.50 | 0.78 | 6.20 | 0.84 | 5.95 | 0.81 |
| 628A | FAA + 2.5 wt. % X-V-1 | 10.44 | 0.96 | 9.76 | 0.98 | 2.92 | 0.50 |
| 628A | FAA + 2.5 wt. % X-V-1 | | | 9.85 | 0.97 | 3.45 | 0.50 |

TABLE 13-continued

Binding capacities of phosphonic, carboxylic, and sulfonic polymers

| Sample Name | Description | Total mmoles (Na$^+$ + K$^+$) bound/gm resin, pH 12.5 | Na$^+$:K$^+$ ratio at pH 12.5 | Total mmoles (Na$^+$ + K$^+$) bound/gm resin, pH 6.25 | Na$^+$:K$^+$ ratio at pH 6.25 | Total mmoles (Na$^+$ + K$^+$) bound/gm resin, pH 3 | Na$^+$:K$^+$ ratio at pH 3 |
|---|---|---|---|---|---|---|---|
| 628B | FAA + 5.0 wt. % X-V-1 | 10.22 | 1.01 | 9.61 | 1.01 | 2.93 | 0.48 |
| 628C | FAA + 10 wt. % X-V-1 | 10.05 | 1.02 | 9.36 | 1.02 | 2.84 | 0.47 |
| 628C | FAA + 10 wt. % X-V-1 | 10.68 | 0.98 | 9.18 | 0.97 | 2.85 | 0.42 |
| 628C | FAA + 10 wt. % X-V-1 | 9.87 | 0.93 | 9.63 | 0.85 | 2.13 | 0.27 |
| 628D | FAA + 20 wt. % X-V-1 | 9.12 | 1.03 | 8.52 | 1.02 | 2.59 | 0.50 |
| 629A | FAA + 25 mol % NaOH + 12.5 wt. % X-V-1 | 9.59 | 1.02 | 9.18 | 1.00 | 2.87 | 0.44 |
| | | 10.27 | 0.99 | 9.52 | 0.98 | 2.79 | 0.41 |
| 629B | FAA + 50 mol % NaOH + 12.5 wt. % X-V-1 | 9.58 | 1.02 | 9.05 | 1.02 | 2.69 | 0.38 |
| 629B | FAA + 50 mol % NaOH + 12.5 wt. % X-V-1 | 10.06 | 0.93 | 9.01 | 0.85 | 1.68 | 0.14 |
| 629C | FAA + 75 mol % NaOH + 12.5 wt. % X-V-1 | 9.41 | 0.98 | 9.33 | 1.01 | 3.19 | 0.54 |
| 629D | FAA + 100 mol % NaOH + 12.5 wt. % X-V-1 | 9.55 | 0.98 | 9.43 | 1.00 | 3.05 | 0.54 |
| 636A2 | NaVSA + 5 wt. % X-V-3 | | | 6.43 | 0.72 | 7.15 | 0.75 |
| 636A3 | NaVSA + 10 wt. % X-V-3 | 7.93 | 0.77 | 6.70 | 0.76 | 7.07 | 0.77 |
| 636A4 | NaVSA + 20 wt. % X-V-3 | 7.41 | 0.76 | 6.29 | 0.76 | 6.28 | 0.75 |
| 636B3 | NaVSA + 10 wt. % X-V-3 | 9.52 | 0.81 | 6.49 | 0.74 | 7.03 | 0.77 |
| 636B4 | NaVSA + 20 wt. % X-V-3 | 7.76 | 0.79 | 6.10 | 0.77 | 6.53 | 0.78 |
| 639A | FAA + 10 wt. % X-V-1 | 9.72 | 0.92 | 8.75 | 0.84 | 3.20 | 0.41 |
| 639A | FAA + 10 wt. % X-V-1 | 10.38 | 0.90 | 9.45 | 0.85 | 1.92 | 0.22 |
| 639B | FAA + 50 mol % NaOH + 12.5 wt. % X-V-1 | 8.97 | 0.92 | 8.85 | 0.85 | | |
| 639B | FAA + 50 mol % NaOH + 12.5 wt. % X-V-1 | 9.46 | 0.95 | 8.68 | 0.83 | 1.73 | 0.17 |
| 639B | FAA + 50 mol % NaOH + 12.5 wt. % X-V-1 | 8.447 | 0.87 | 8.192 | 0.834 | | |
| 616B3 | NaVSA + 20 wt. % X-V-1 | 5.87 | 0.71 | 6.14 | 0.72 | 6.57 | 0.78 |
| 100851A2 | purified NaVSA + 5 wt. % X-V-1 | 5.92 | 0.67 | 6.68 | 0.70 | 5.58 | 0.69 |
| 100851A2 | purified NaVSA + 5 wt. % X-V-1 | 7.42 | 0.79 | 7.08 | 0.74 | 5.99 | |
| 100851A2 | purified NaVSA + 5 wt. % X-V-1 | 6.57 | 0.77 | 6.45 | 0.71 | 5.87 | 0.74 |
| 100851A3 | purified NaVSA + 10 wt. % X-V-1 | 6.27 | 0.07 | 6.84 | 0.72 | 6.17 | 0.72 |
| 100851A3 | purified NaVSA + 10 wt. % X-V-1 | 6.97 | 0.75 | 7.50 | 0.74 | 6.78 | 0.77 |
| 100851A4 | purified NaVSA + 20 wt. % X-V-1 | 5.84 | 0.71 | 6.53 | 0.73 | 5.21 | 0.70 |
| 100851A4 | purified NaVSA + 20 wt. % X-V-1 | 6.28 | 0.81 | 6.28 | 0.75 | | |
| 100851A4 | purified NaVSA + 20 wt. % X-V-1 | 6.22 | 0.76 | 6.82 | 0.75 | 5.48 | 0.74 |
| 100851B1 | purified NaVSA + 2.5 wt. % X-V-5 | 6.42 | 0.65 | 6.50 | 0.65 | 6.09 | 0.65 |
| 100851B2 | purified NaVSA + 5 wt. % X-V-5 | 5.76 | 0.62 | 6.72 | 0.64 | 6.27 | 0.65 |
| 100851B2 | purified NaVSA + 5 wt. % X-V-5 | 6.77 | 0.73 | 7.27 | 0.67 | 6.48 | 0.71 |
| 100851B3 | purified NaVSA + 10 wt. % X-V-5 | 5.83 | 0.61 | 7.07 | 0.64 | 5.57 | 0.60 |
| 100851B3 | purified NaVSA + 10 wt. % X-V-5 | 6.66 | 0.80 | 7.27 | 0.69 | 6.05 | 0.68 |
| 100851B4 | purified NaVSA + 20 wt. % X-V-5 | 6.50 | 0.65 | 6.25 | 0.61 | 5.22 | 0.59 |
| 100851B4 | purified NaVSA + 20 wt. % X-V-5 | 5.50 | 0.66 | 6.59 | 0.66 | 5.82 | 0.66 |
| 100851C2 | purified NaVSA + 5 wt. % X-V-1 | 6.52 | 0.70 | 6.40 | 0.68 | 5.52 | 0.67 |
| 100851C2 | purified NaVSA + 5 wt. % X-V-1 | 7.23 | 0.78 | 7.03 | 0.75 | | |
| 100851C3 | purified NaVSA + 10 wt. % X-V-1 | 6.77 | 0.72 | 7.02 | 0.72 | 5.90 | 0.71 |
| 100851C4 | purified NaVSA + 20 wt. % X-V-1 | 6.05 | 0.72 | 6.08 | 0.71 | 4.66 | 0.68 |
| 100851C4 | purified NaVSA + 20 wt. % X-V-1 | 6.51 | 0.78 | 8.07 | 0.80 | | |
| 100851D1 | purified NaVSA + 2.5 wt. % X-V-5 | 7.07 | 0.74 | 7.28 | 0.71 | 5.87 | 0.69 |
| 100851D1 | purified NaVSA + 2.5 wt. % X-V-5 | 7.65 | 0.73 | 7.40 | 0.72 | | |
| 100851D2 | purified NaVSA + 5 wt. % X-V-5 | 6.83 | 0.66 | 7.17 | 0.71 | 5.42 | 0.64 |
| 100851D2 | purified NaVSA + 5 wt. % X-V-5 | 7.91 | 0.75 | 7.37 | 0.70 | | |
| 100851D3 | purified NaVSA + 10 wt. % X-V-5 | 6.70 | 0.67 | 6.87 | 0.66 | 5.21 | 0.64 |
| 100851D4 | purified NaVSA + 20 wt. % X-V-5 | 6.24 | 0.67 | 6.46 | 0.67 | 6.63 | 0.58 |
| 100851D4 | purified NaVSA + 20 wt. % X-V-5 | 7.01 | 0.68 | 6.61 | 0.70 | | |
| 100982A1 | FAA + 10 wt. % X-V-1 | 9.66 | 0.89 | 9.02 | 0.86 | 3.40 | 0.50 |
| 100982A1 | FAA + 10 wt. % X-V-1 | | | 8.47 | 0.86 | | |
| 100982A2 | 90 wt. % FAA + 10 wt. % acrylic acid + 10 wt. % X-V-1 | 9.81 | 0.92 | 8.49 | 0.86 | 2.98 | 0.52 |
| 100982A2 | 90 wt. % FAA + 10 wt. % acrylic acid + 10 wt. % X-V-1 | | | 8.00 | 0.86 | | |
| 100982A3 | 80 wt. % FAA + 20 wt. % acrylic acid + 10 wt. % X-V-1 | 10.00 | 0.95 | 7.97 | 0.86 | 2.89 | 0.56 |
| 100982A3 | 80 wt. % FAA + 20 wt. % acrylic acid + 10 wt. % X-V-1 | | | 7.74 | 0.87 | | |
| 100982A4 | 70 wt. % FAA + 30 wt. % acrylic acid + 10 wt. % X-V-1 | 9.92 | 0.97 | 8.52 | 0.85 | 2.42 | 0.54 |
| 100982A4 | 70 wt. % FAA + 30 wt. % acrylic acid + 10 wt. % X-V-1 | | | 7.49 | 0.88 | | |
| 100982A5 | 60 wt. % FAA + 40 wt. % acrylic acid + 10 wt. % X-V-1 | 10.00 | 1.00 | 7.48 | 0.86 | 2.01 | 0.53 |
| 100982A5 | 60 wt. % FAA + 40 wt. % acrylic acid + 10 wt. % X-V-1 | | | 7.10 | 0.89 | | |
| 100982A6 | 50 wt. % FAA + 50 wt. % acrylic acid + 10 wt. % X-V-1 | 10.41 | 1.03 | 7.56 | 0.87 | 2.11 | 0.61 |

TABLE 13-continued

Binding capacities of phosphonic, carboxylic, and sulfonic polymers

| Sample Name | Description | Total mmoles ($Na^+ + K^+$) bound/gm resin, pH 12.5 | $Na^+$:$K^+$ ratio at pH 12.5 | Total mmoles ($Na^+ + K^+$) bound/gm resin, pH 6.25 | $Na^+$:$K^+$ ratio at pH 6.25 | Total mmoles ($Na^+ + K^+$) bound/gm resin, pH 3 | $Na^+$:$K^+$ ratio at pH 3 |
|---|---|---|---|---|---|---|---|
| 100982A6 | 50 wt. % FAA + 50 wt. % acrylic acid + 10 wt. % X-V-1 | | | 7.11 | 0.90 | | |
| 101012A1 | purified NaVSA + 2.5 wt. % X-V-2 | | | | | | |
| 101012A2 | purified NaVSA + 5 wt. % X-V-2 | 7.50 | 0.74 | 7.70 | 0.74 | 6.49 | 0.74 |
| 101012A3 | purified NaVSA + 10 wt. % X-V-2 | 7.04 | 0.74 | 7.31 | 0.74 | 6.27 | 0.74 |
| 101012A4 | purified NaVSA + 20 wt. % X-V-2 | 6.52 | 0.75 | 6.88 | 0.75 | 6.01 | 0.76 |
| 101012B1 | purified NaVSA + 2.5 wt. % X-V-4 | | | | | | |
| 101012B2 | purified NaVSA + 5 wt. % X-V-4 | 7.53 | 0.71 | 7.64 | 0.71 | 6.93 | 0.72 |
| 101012B3 | purified NaVSA + 10 wt. % X-V-4 | 6.88 | 0.70 | 7.19 | 0.71 | 6.24 | 0.70 |
| 101012B4 | purified NaVSA + 20 wt. % X-V-4 | 6.34 | 0.68 | 6.78 | 0.70 | 6.08 | 0.70 |
| 101012D1 | purified NaVSA + 2.5 wt. % X-V-7 | 7.02 | 0.73 | 6.68 | 0.73 | 4.86 | 0.67 |
| 101012D2 | purified NaVSA + 5 wt. % X-V-7 | 7.35 | 0.74 | 7.24 | 0.74 | 6.58 | 0.73 |
| 101012D3 | purified NaVSA + 10 wt. % X-V-7 | 7.17 | 0.74 | 7.30 | 0.74 | 6.64 | 0.75 |
| 101012D4 | purified NaVSA + 20 wt. % X-V-7 | 6.33 | 0.72 | 6.64 | 0.74 | 5.83 | 0.74 |
| 101028A1 | purified NaVSA + 10 wt. % X-V-1 | 6.47 | 0.76 | 5.69 | 0.75 | 5.47 | 0.77 |
| 101028A2 | 90 wt. % purified NaVSA + 10 wt. % FAA + 10 wt. % X-V-1 | 6.67 | 0.81 | 6.01 | 0.79 | 4.67 | 0.72 |
| 101028A3 | 80 wt. % purified NaVSA + 20 wt. % FAA + 10 wt. % X-V-1 | 7.17 | 0.82 | 6.50 | 0.80 | 4.25 | 0.68 |
| 101028A4 | 70 wt. % purified NaVSA + 30 wt. % FAA + 10 wt. % X-V-1 | 7.33 | 0.84 | 6.77 | 0.81 | 4.12 | 0.66 |
| 101028A5 | 60 wt. % purified NaVSA + 40 wt. % FAA + 10 wt. % X-V-1 | 7.69 | 0.85 | 7.00 | 0.83 | 3.43 | 0.60 |
| 101028A6 | 50 wt. % purified NaVSA + 50 wt. % FAA + 10 wt. % X-V-1 | 8.25 | 0.87 | 7.29 | 0.85 | 3.80 | 0.63 |
| 101029A2 | VPA + 5 wt. % X-V-1 | | | | | | |
| 101029A3 | VPA + 10 wt. % X-V-1 | 11.38 | 1.49 | 5.70 | 1.00 | 2.37 | 0.89 |
| 101029A4 | VPA + 20 wt. % X-V-1 | 10.15 | 1.66 | 4.90 | 1.03 | 2.27 | 0.88 |
| 101029B2 | VPA + 50 mol % NaOH + 5 wt. % X-V-1 | | | | | | |
| 101029B3 | VPA + 50 mol % NaOH + 10 wt. % X-V-1 | 10.97 | 1.50 | 5.27 | 0.98 | 2.63 | 0.91 |
| 101029B4 | VPA + 50 mol % NaOH + 20 wt. % X-V-1 | 10.23 | 1.62 | 5.10 | 1.01 | 2.06 | 0.88 |
| 684A | FAA + 5 wt. % X-V-1 | 10.7 | 0.91 | 10.30 | 0.84 | nm | nm |
| 684B | FAA + 5 wt. % X-V-1 | 9.80 | 0.83 | 9.70 | 0.82 | nm | nm |
| | Dowex 50WX4-200 (average of 15 experiments) | 5.37 | 0.77 | 5.51 | 0.77 | 4.92 | 0.76 |
| | Dowex 50W (Standard deviation of 15 experiments) | 0.77 | 0.06 | 0.81 | 0.08 | 0.80 | 0.06 | nm: not measured

These examples show that the polymers of the invention display high potassium binding capacity at physiological pHs. In particular polymers prepared from 2-fluoroacrylic acid can bind up to two times more potassium than sulfonated polystyrene resins Dowex.

Example 3

Procedure for Predicting Binding of Cations in the Human GI

This procedure was used to model the conditions of use of a potassium binder drug and measure the binding characteristics of the polymer for potassium (target solute) in the presence of other competing cations. A meal mimic was prepared and artificially digested in the presence of pepsin and pancreatic juice. The sequence of addition of enzymes and the pH profile were controlled so that the digestion process was simulated down to the jejunum level. The test polymers, preloaded with lithium, were added to the digested meal mimic and allowed to equilibrate for a fixed period of time; the mixture was then centrifuged and the supernatant was assayed for $Na^+$, $K^+$, $NH_4^+$, $Ca^{2+}$, and $Mg^{2+}$ by ion chromatography. The lithium released was computed as the total cation exchange, while the decrease in concentrations of the other cations was used to compute their binding variations in western diets.

Preparation of Resin

Resin (test resin, or Dowex 50WX4-200 used as a comparative), was washed extensively in 1M HCl to convert it to the H-form. It was then washed extensively in 1M LiOH. Excess LiOH was removed by washing in ddH$_2$O. The resins were lyophilized and stored in a desiccator.

Figure 2:
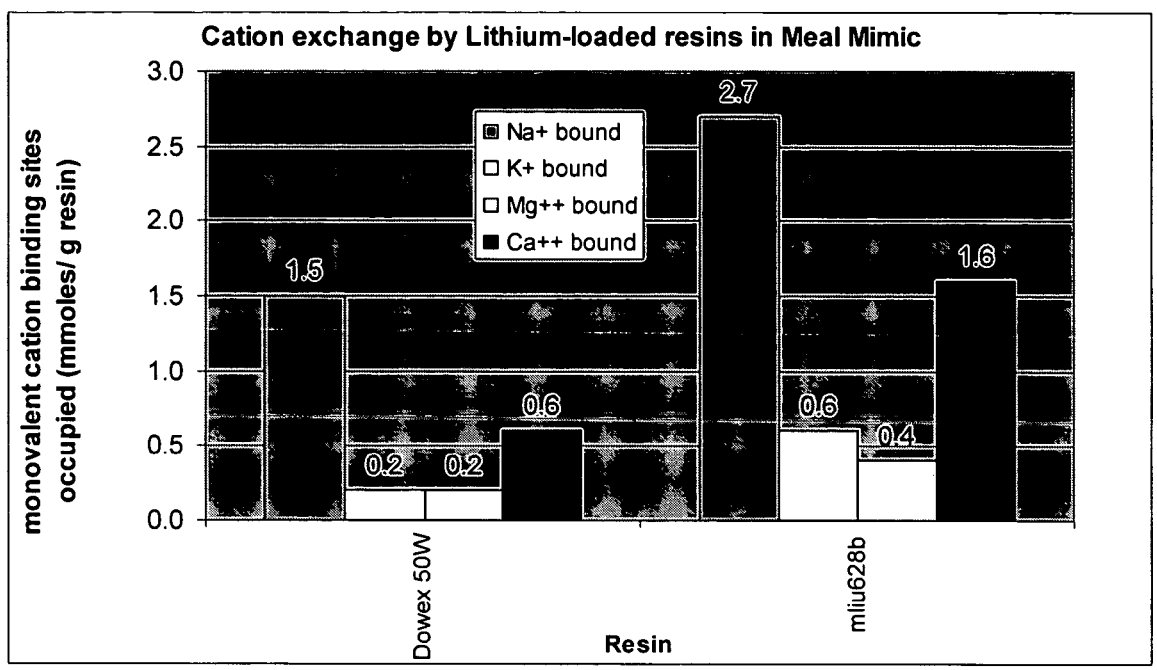
FIG. 2 depicts binding of cations by resins in a meal mimic.

FIG. 1 depicts starting cation concentrations in meal mimic and FIG. 2 depicts binding of cations by resins in meal mimic.

Measurement of Binding Capacities in Cecal and Fecal Extracts

Two volumes (w/v) of ice-cold ddH$_2$O were added to the human feces and to normal rabbit cecal contents. These were incubated with rotation at 4° C. with end-over-end rotation for at least 1 hour to extract soluble cations. Fecal and cecal extracts, as well as thawed meal mimics, were centrifuged at 2000 g for 10 minutes to clarify. Approximately 50 mg Li-form Dowex 50W was weighed into 16×100 mm glass test tubes. Control test tubes were included that contained no resin. Clarified extracts or mimics were added to a final resin concentration of 2.5 mg/ml. 5-10 ml of extracts or mimic were added to the control test tubes. Tubes were sealed and rotated at 4° C. for 90 minutes. The tubes were centrifuged at 500 g for thirty minutes to precipitate the resin. Supernatant samples were taken. The samples were then prepared for ion chromatography by spinning at 13,000 g for ten minutes, taking the supernatant and rapidly passing across a 3000 Da cutoff dialysis membrane by centrifugation. Extracts were further diluted 1:5 (v/v) in ddH$_2$O before applying to the IC columns. Start (without resin) and equilibrium (with resin) concentrations of Li$^+$, Na$^+$, K$^+$, NH$_4^+$, Ca$^{++}$ and Mg$^{++}$ were determined, and the amount (in mmoles cation/gm resin) of Li$^+$ released, as well as Na$^+$, K$^+$, NH$_4^+$, Ca$^{++}$ and Mg$^{++}$ bound were calculated.

Procedure for Measuring the Binding of Cations by Resins in Human Fecal Extracts Resins and feces were prepared as follows. Resins were washed extensively in 1M HCl to convert them to the H-form. Excess HCl was removed by washing in ddH$_2$O. The resins were lyophilized and stored in a desiccator. Fecal samples were obtained from two human subjects, frozen immediately and stored at −80° C. to minimize ammonium production ex vivo.

Figure 3:
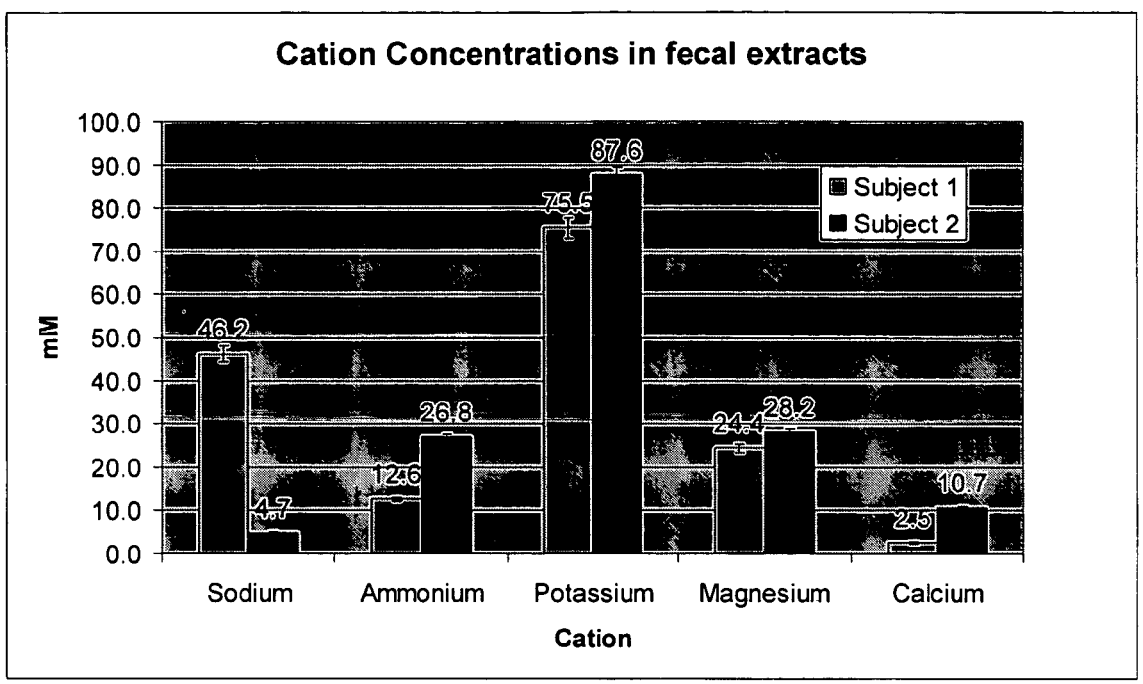
FIG. 3 depicts the original concentrations of cations in the feces of two subjects.
Figure 4:
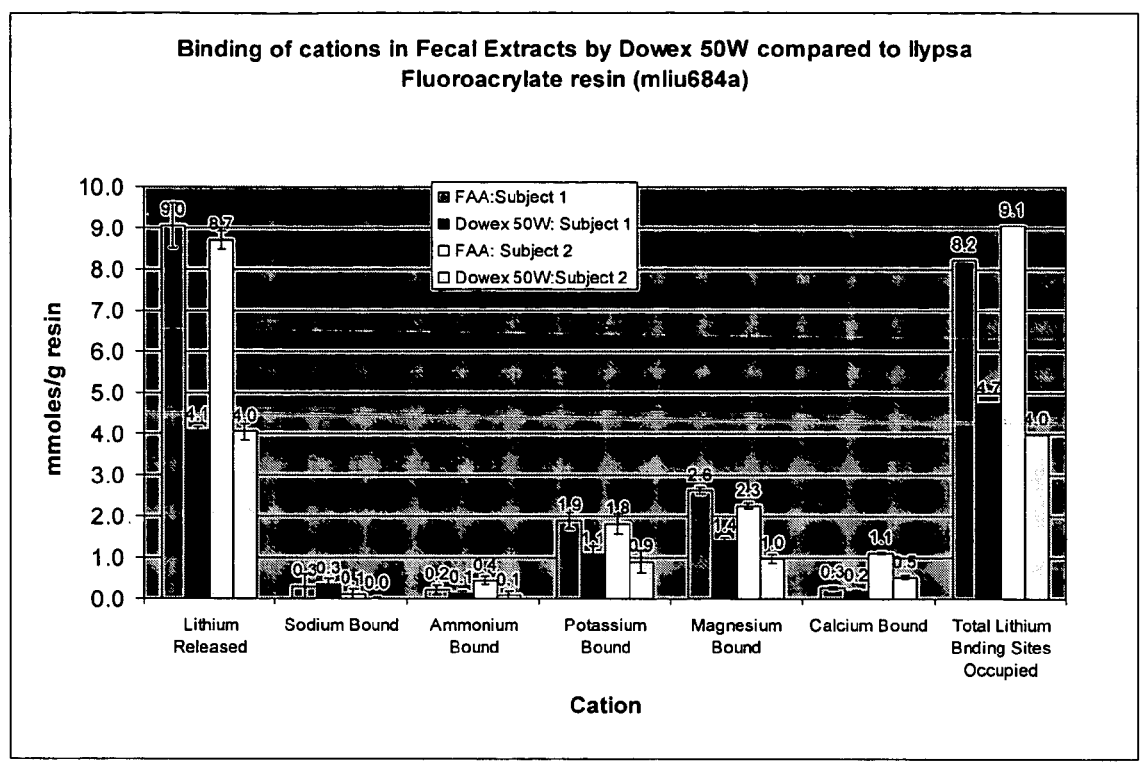
FIG. 4 depicts the binding of cations in human fecal extracts to cation exchange resins.

All experiments were performed in triplicate. Error bars on FIGS. 3 and 4 indicate standard deviations values. Fecal samples were resuspended in two volumes of ice-cold ddH$_2$O (w/v) and incubated overnight at 4° C. to extract soluble cations. The extract was then clarified by centrifuging at 2000 g for ten minutes. H-form resins were weighed into disposable 15 ml-capacity columns. They were them washed extensively in 150 mM LiOH to convert them to the Li-form. They were washed in ddH$_2$O to remove excess LiOH. Clarified fecal extract was applied to the columns to a final resin concentration of 2.5 mg/ml of extract. A sample was retained for calculating resin concentrations in the absence of resin. Columns were capped and rotated at 4° C. for three hours. They were then eluted by centrifugation into 50 ml polypropylene tubes. The pH of eluted extracts and retained clarified fecal extracts were measured (it had not changed: Sample 1 pH was 6.75, sample 2 pH was 7.1). The samples were then prepared for ion chromatography by spinning at 13,000 g for ten minutes, taking the supernatant and rapidly passing across a 3000 Da cutoff dialysis membrane by centrifugation. Extracts were further diluted 1:5 (v/v) in ddH$_2$O before applying to the IC columns. Start (without resin) and equilibrium (with resin) concentrations of Li$^+$, Na$^+$, K$^+$, NH$_4^+$, Ca$^{++}$ and Mg$^{++}$ were determined, and the amount (in mmoles cation/gm resin) of Li$^+$ released, as well as Na$^+$, K$^+$, NH$_4^+$, Ca$^{++}$ and Mg$^{++}$ bound were calculated. In FIG. 4 "Total occupied" refers to the sum of Li$^+$ (i.e. monovalent) binding sites occupied by the other cations, taking into account the divalent nature of Ca$^{++}$ and Mg$^{++}$.

Data presented in FIG. 4 demonstrate that the ex-vivo binding of potassium in human fecal extracts for the FAA based material is about twice as much that of Dowex 50WX4-200 (a material essentially identical in composition to the potassium binder Kayexalate). The ex-vivo binding of potassium by the Dowex resin is essentially the same as that reported for polystyrene sulfonate resins in human clinical studies, which establishes this method as a good predictor for in-vivo binding performance. It also indicates that other cations, in particular Magnesium and Calcium, compete with potassium for the binding sites of the polymers. FIG. 3 depicts the original concentrations of cations in the Feces of Subject 1 and Subject 2. FIG. 4 depicts the binding of cations in human fecal extracts to cation exchange resins.

Example 4

Method of Selection of Semi-permeable Membrane with High Potassium Binding Selectivity Over Magnesium and Calcium This protocol describes a method to optimize polymeric materials with regards to their ion permselectivity characteristics, which then can be used as the shell component for the making of potassium selective core-shell ion-exchange particles.

Polymer Synthesis and Membrane Preparation:

Polymeric membrane materials with different compositions were prepared by radical copolymerization of DBA (N,N'-dibutyl acrylamide) and DEAEMA (N,N'-diethylaminoethylmethacrylate) in a glove box using miniaturized reactors in a library format. AIBN was used as the initiator and ethanol as the solvent. Polymers were isolated by precipitation into water, freeze-dried, and characterized by GPC and H-NMR. The composition of the polymer (DBA mol %) ranges from 30% to 70% and molecular weight ranges from 200K to 300K as shown below:

TABLE 14

| | Polymer ID 101224 | | | | | |
|---|---|---|---|---|---|---|
| | D1 | D2 | D3 | D4 | D5 | D6 |
| Mn (×10$^3$) | 327 | 326 | 322 | 285 | 240 | 217 |
| Mw (×10$^3$) | 584 | 563 | 520 | 467 | 411 | 340 |
| PDI | 1.78 | 1.73 | 1.61 | 1.64 | 1.71 | 1.56 |
| Composition (DBA, mol %) | 31.2 | 37.1 | 48.5 | 56.1 | 64.4 | 68.5 |

Polymer membranes were prepared by casting a 2-wt % toluene solution of DBA-co-DEAEMA onto a regenerated cellulose dialysis membrane (RC membrane with MWCO of 14 K). After toluene was evaporated, a polymer membrane was formed on the top of dialysis membrane. A composite membrane of polymer membrane and RC membrane was thus prepared.

Permeability Study on Cations

Figure 5:
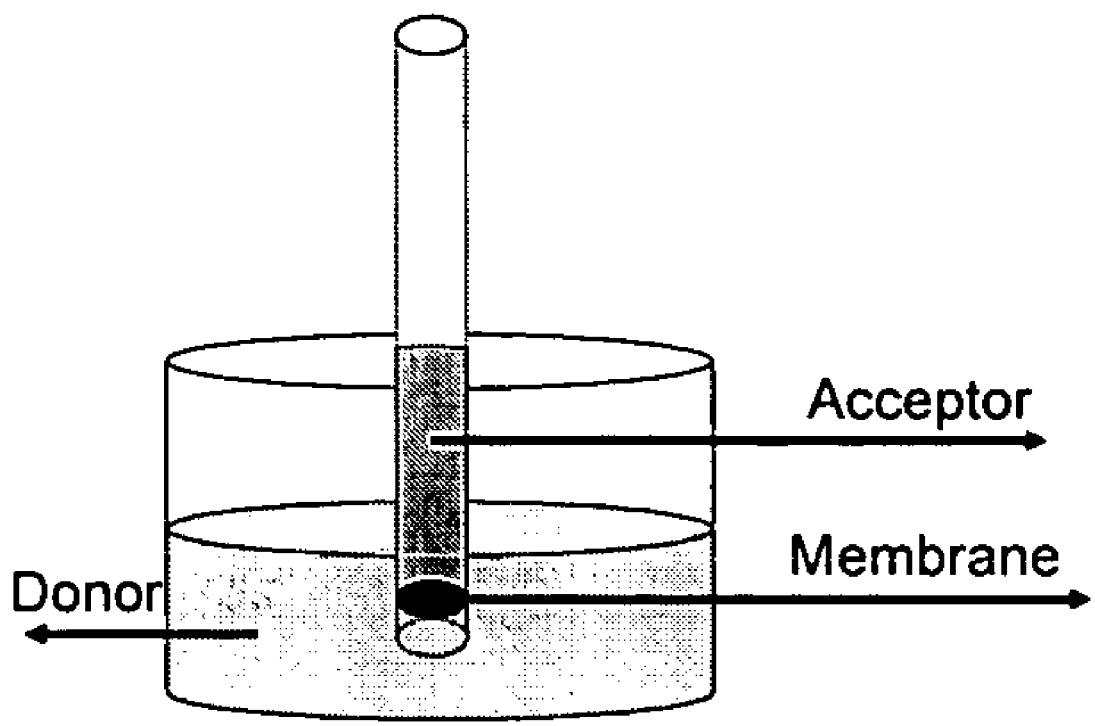
FIG. 5 depicts the membrane preparation for determination of ion permeability.

The composite membrane was first clamped onto a glass tube with diameter of 13 mm, and then immersed into a 2 L of donor solution of cations. The tube was filled with 10 ml of acceptor solution (lactose solution with the same osmolality as the donor solution (240 mM)). The acceptor solution was sampled at a specified time interval and analyzed by ion chromatography. See FIG. 5.

Donor solution was prepared by mixing the aqueous solution of NaCl, KCl, CaCl$_2$.2H$_2$O, and MgSO$_4$.7H$_2$O. The solution was buffered to pH 6 by using 14 mM of MES (2-[N-morpholine]ethanesulfonic acid]solution. The concentrations of different cations determined by IC were as follows: [Na$^+$], 40.46 mM; [K$^+$], 31.44 mM; [Mg$^{2+}$], 33.25 mM; [Ca$^{2+}$], 22.324 mM.

Determination of the permeability coefficient (P) of different cations: As mentioned in the measurement set-up, the acceptor solution was sampled at a specific time interval and analyzed by IC. Assuming a Fick's first law of diffusion, P is readily obtained by linearization of the data, following a method of calculation reported in equation 1 in G. Van den Mooter, C. Samyn, and R. Kinget, International Journal of Pharmaceutics, 111, 127-136(1994). The permeability coefficients of different cations were thus calculated from the slope from this linear relationship.

$$-\ln\left(\frac{C_o - C_a}{C_o}\right) = \frac{PS}{Va} t \qquad \text{Equation 1}$$

Where $C_o$ is the initial concentration of the solute in the donor compartment and $C_a$ the concentration in the acceptor compartment at time t, Va is the volume of the acceptor compartment, and S the surface of the membrane.

Permselectivity: As described above, the permeability coefficient was calculated for each cation. By normalizing the permeability coefficient of $Na^+$ as 1, the permselectivity for cations M1 and M2 can be calculated as follows: $P_{M1}{}^{M2}$=P(M2)/P (M1)

Permeability Coefficients of Different Cations Through Different Membranes:

Table 14 shows the permeability coefficients of different cations at different membranes. When polymers are more hydrophilic (Polymer D3 and D4 with DBA % 48.5 and 56.1%, respectively), all cations, such as $Na^+$, $K^+$, $Mg^{2+}$, and $Ca^{2+}$, are more permeable and their permeability coefficients are comparable to those through a blank dialysis membrane (RC membrane) and reflect the self-diffusivity of the cations. However, with the increasing DBA content in polymer membrane (See Table 15 for D5 and D6), the permeability coefficients of different cations decreased as compared with blank membrane, which means that the hydrophobic nature of polymer membrane could make cations less permeable through the hydrophobic barrier.

TABLE 15

Permeability coefficients of cations at different membranes

| Polymer ID | DBA (mol %) | $PNa^+$ (cm/sec) | $PK^+$ (cm/sec) | $PMg^{2+}$ (cm/sec) | $PCa^{2+}$ (cm/sec) |
|---|---|---|---|---|---|
| D3 | 48.5 | 2.41(±0.26)E−4 | 3.11(±0.34)E−4 | 6.50(±0.08)E−5 | 6.0(±0.07)E−5 |
| D4 | 56.1 | 4.28(±0.44)E−5 | 6.11(±0.61)E−4 | 1.13(±0.11)E−5 | 1.04(±0.05)E−5 |
| D5 | 64.4 | 4.32(±0.20)E−6 | 5.79(±3.59)E−6 | 5.42(±4.11)E−7 | 3.32(±3.33)E−7 |
| D6 | 68.5 | 1.50(±0.05)E−7 | — | — | — |

Another characteristic for the permeability of different cations is their permselectivity. By normalizing the value of $P_{Na+}$ as 1, the permselectivity for other cations can be calculated and the results are shown in Table 16. The permselectivity of $P_{Mg}/P_{Na}$ and $P_{Ca}/P_{Na}$ decreases with the increasing DBA content in polymer membranes, which implies that more hydrophobic polymer membranes may have better selectivity for different cations. For a better selectivity for different cations, two factors should be considered—the charge density and the membrane hydrophobicity.

TABLE 16

| Polymer ID | DBA (%) | $P(K^+)/P(Na^+)$ | $P(Ca^{2+})/P(Na^+)$ | $P(Mg^{2+})/P(Na^+)$ | $P(K^+)/P(Mg^{2+})$ |
|---|---|---|---|---|---|
| D3 | 48.5 | 1.29 | 0.27 | 0.25 | 5.16 |
| D4 | 56.1 | 1.43 | 0.26 | 0.24 | 5.96 |
| D5 | 64.4 | 1.34 | 0.13 | 0.08 | 16.75 |

Example 5

Synthesis of poly-2-fluoroacrylic Acid Beads

Beads are prepared by a direct suspension process where a mixture of 2-fluoroacrylic methyl ester/divinylbenzene/benzoyl peroxide in a weight ratio 90/9/1 are dispersed in water under high shear with polyvinylalcohol as a suspending agent. The suspension is stirred and heated at 80° C. for 10 hours. The residual monomer is eliminated by steam stripping. The beads are then filtered and treated with aqueous 3M NaOH to hydrolyze the polymer, then washed, treated with HCL, water-washed, and finally dried to form the desired poly$\alpha$-fluoroacrylic acid particles. The average bead diameter is 250 microns as measured by Master Sizer (Malvern UK).

Example 6

Preparation of poly-2-fluoroacrylic Acid/Core-(DBA-DEAEMA)/Shell Particles

The core-shell particles are prepared by forming a coating of polymer D2 on the poly-2-fluoroacrylic acid beads prepared in example 5 using a Wurster coater. The shell polymer prepared in example 4 is first dissolved at 20 wt-% in toluene, and the thus obtained solution then dispersed in water in a 1:4 weight ratio with 2 wt-% based on the organic phase of CTAB (Hexadecyltrimethyl-Ammonium Bromide) as a surfactant, using a Ultra-Turrax high-shear homogeneizer. The toluene is then driven off by evaporation under reduced pressure. The average diameter of the dispersion particles is 0.3 micrometer, as measured by Dynamic Light Scattering. The poly-2-fluoroacrylic acid beads are spray-coated with the shell polymer dispersion using a Wurster fluid bed coater 2"-4"/6" Portable Unit. The fluidized bed unit is operated so that an average 5 microns thick coating is deposited on the core particles.

The potassium binding capacity when measured in a fecal extract as described in Example 3 is expected to be twice higher than that measured with the uncoated poly-$\alpha$-fluoroacrylic acid beads.

Example 7

Preparation of Polystyrene Sulfonate/Core-polyethyleneimine Shell Particles with $Na^+$ and $K^+$ Selective-binding Propertie Procedure for Coating PEI on Dowex Beads PEI (poly(ethyleneimine), Mw10,000) and Dowex beads (H-form, X4-200) were purchased from commercial sources.

PEI aqueous solutions with different concentrations were prepared by dissolving PEI directly into nanopure water.

Weighed dried Dowex beads were mixed with PEI aqueous solution in library format glass tubes. After a specified reaction time, the tubes were sealed and centrifuged at 1000 rpm for 15 minutes, the supernatant solutions were then decanted off. To the beads in each tube was added nanopure water to a total volume of 10 ml and all tubes were sealed and tumbled for 30 minutes. The same tumbling-centrifuging was repeated 3 times. The beads were freeze-dried and weighted until a constant weight was obtained.

The reaction solution composition and gel weight increase are displayed in Table 17.

TABLE 17

Conditions for coating PEI on Dowex beads

| Dowex Bead Weight (gm) | PEI Conc. (wt %) | PEI volume (ml) | Reaction time (hours) | Coated bead ID | Weight increase (Δwt %) |
|---|---|---|---|---|---|
| 0.1274 | 2.5 | 10 | 1 | DOWEX(2.5 wt-1 h) | * |
| 0.2223 | 2.5 | 10 | 6 | DOWEX(2.5 wt-6 h) | 3.1 |
| 0.1609 | 1.5 | 10 | 1 | DOWEX(2.5 wt-1 h) | * |
| 0.2407 | 1.5 | 10 | 6 | DOWEX(2.5 wt-6 h) | 0.9 |
| 0.2016 | 0.5 | 10 | 1 | DOWEX(2.5 wt-1 h) | * |
| 0.2347 | 0.5 | 10 | 6 | DOWEX(2.5 wt-6 h) | * |

* No weight increase was observed.

Method for Binding Study

A mixture of NaCl, KCl, $MgCl_2$, and $CaCl_2$ was dissolved in a MES buffer (pH6.0) (MES, 2-[N-morpholine]ethanesulfonic acid]. The concentration for each cation was determined by IC. The concentrations for $Na^+$, $K^+$, $Mg^{2+}$, and $Ca^{2+}$ are 26.4 mM, 9.75 mM, 4.75 mM and 4.16 mM respectively.

Figure 6:
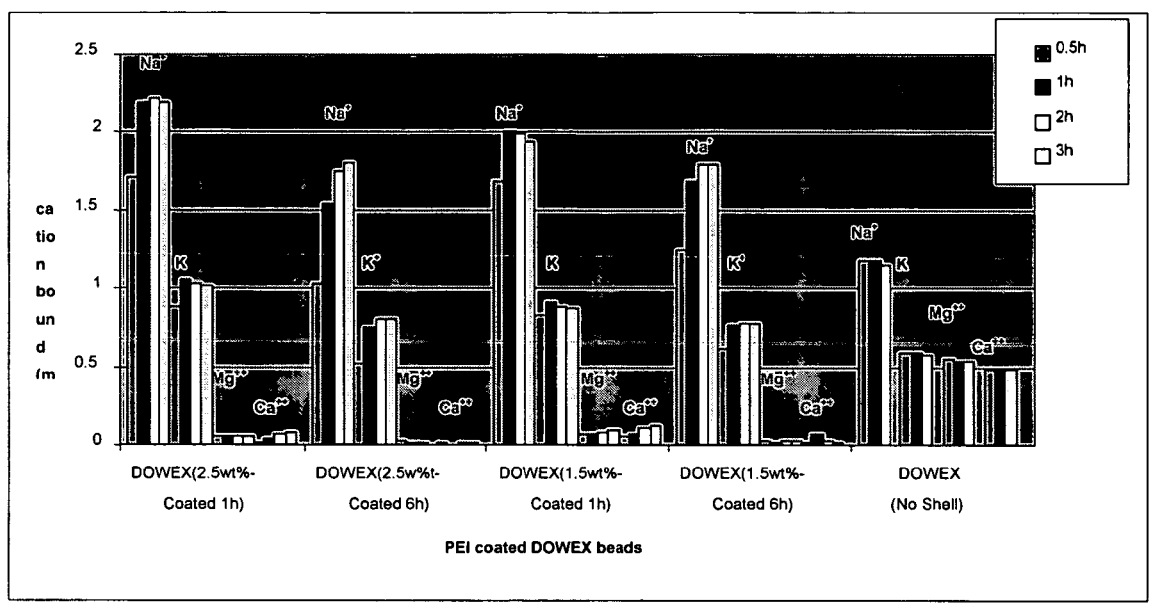
FIG. 6 depicts the binding data of different polyethyleneimine coated beads for different cations.

Weighed dried PEI-coated bead was put into a tube which contains 5-ml of MES buffer solution of NaCl, KCl, $MgCl_2$, and $CaCl_2$. The tube was sealed and tumbled. After a certain period of time as indicated in FIG. 6, the tube was centrifuged. 100 microliter of solution was then taken out from the supernatant for IC analysis. The binding amount of PEI coated beads for different cations were calculated from the concentration change in the solution. The calculation is as follows:

Ion bound in beads(mmol/g)=$[V \times (C_0-C_t)/\{[weight of beads] \times 1000\}]$ $C_0$: initial concentration of metal ion (in mM)
$C_t$: concentration of metal ion after bead binding at a certain time (t hrs) (in mM)
V: solution volume (5 ml)
Weight of beads (gm)

The binding data of different PEI coated beads for different cations are shown in FIG. 6. PEI coated Dowex beads show higher $Na^+$ and $K^+$ binding than the uncoated beads (bare beads). The coated beads show much more selective binding than bare beads. The thicker the PEI coating (e.g. Dowex (2.5 wt-6 h), coated from 2.5 wt % PEI solution for 6 hours), the more selective for the different cations. The binding kinetic study shows that the binding of cations equilibrates faster for the thinner coated beads and bare beads.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All publications, patents, and patent applications mentioned in this specification are herein incorporated by reference to the same extent as if each individual publication, patent, or patent application was specifically and individually indicated to be incorporated by reference.

What is claimed is:

1. A method of treating hyperkalemia in an animal subject, the method comprising
administering to said animal subject an effective amount of a potassium-binding, cation-exchange polymer, the cation-exchange polymer comprising at least one polymer selected from a crosslinked carboxylic polymer, a crosslinked sulfonic polymer, a crosslinked sulfamic polymer, a crosslinked phosphonic polymer, and an anhydride thereof, the crosslinked polymer comprising an electron-withdrawing substituent attached to a carbon atom alpha or beta to an acid group of said polymer and being orally administered in a form having a combination of counterions selected from $Ca^{2+}$, $H^+$, $NH_4^+$, and $Na^+$,
whereby the potassium-binding, cation-exchange polymer binds and removes potassium from a gastrointestinal tract of said animal subject.

2. The method of claim 1 wherein the potassium-binding polymer has an in vitro potassium binding capacity of greater than 5 mmol/gm of said polymer at a pH of greater than 5.5.

3. The method of claim 1 wherein the potassium-binding polymer has an average in vivo potassium binding capacity of at least about 1.5 mmol/gm of said polymer.

4. The method of claim 1 wherein said potassium-binding polymer comprises at least one polymer selected from an optionally crosslinked carboxylic polymer, an optionally crosslinked sulfonic polymer, an optionally crosslinked sulfamic polymer, an optionally crosslinked phosphonic polymer, and an anhydride thereof.

5. The method of claim 1 wherein said potassium-binding polymer is a polystyrene sulfonate.

6. The method of claim 1 wherein less than 1% of said potassium-binding polymer is absorbed from the gastrointestinal tract of said animal subject.

7. The method of claim 1 wherein said treatment has a therapeutic or prophylactic benefit.

8. The method of claim 1 wherein said electron-withdrawing substituent is a hydroxyl group, an ether group, an ester group, or a halide group.

9. The method of claim 8 wherein said halide group is fluoride, chloride, or bromide.

10. The method of claim 4 wherein said potassium binding polymer comprises a poly-fluoroacrylic acid polymer, a poly-difluoromaleic acid polymer, or a combination thereof.

11. The method of claim 10 wherein said potassium binding polymer comprises 2-fluoroacrylic acid crosslinked with divinylbenzene, ethylene bisacrylamide, N,N'-bis(vinylsulfonylacetyl) ethylene diamine, 1,3-bis(vinylsulfonyl) 2-propanol, vinylsulfone, N,N'-methylenebisacrylamide, or a combination thereof.

12. The method of claim 11 wherein said potassium binding polymer comprises crosslinked 2-fluoroacrylic polymer or co-polymer, said polymer or co-polymer obtained by polymerization of an alkylester of 2-fluoroacrylic acid with divinylbenzene and followed by ester hydrolysis.

13. The method of claim 1 wherein said potassium-binding polymer is at least one polymer selected from an optionally crosslinked 2-fluroacrylate polymer, an optionally crosslinked vinyl sulfonic acid polymer, and an optionally crosslinked vinyl phosphonic acid polymer.

14. The method of claim 1 wherein the potassium-binding polymer comprises an enteric coating, said coating being capable of disintegrating in a colon.

15. The method of claim 1 wherein said potassium-binding polymer preferentially binds a potassium ion over a competing magnesium ion.

16. The method of claim 1, 2, or 3 wherein said potassium binding polymer is co-administered with a drug that promotes potassium retention.

17. The method of claim 1, 2, or 3 wherein said composition is co-administered with an ACE inhibitor, an angiotensin II receptor blocker (ARB), a potassium sparing diuretic, or any combination thereof.

18. The method of claim 1, 2, or 3 wherein said potassium-binding polymer is combined with at least one pharmaceutically acceptable excipient to form a pharmaceutical formulation.

19. The method of claim 18 wherein said pharmaceutical formulation is an oral formulation, and the cation exchange polymer is a crosslinked polymer comprising a repeat unit having acid groups in protonated, ionized or anhydride form.

20. The method of claim 19 wherein said oral formulation is a liquid formulation or a chewable tablet formulation.

* * * * *